United States Patent [19]
McCormick et al.

[11] Patent Number: 5,763,573
[45] Date of Patent: Jun. 9, 1998

[54] GTPASE ACTIVATING PROTEIN FRAGMENTS

[75] Inventors: Francis P. McCormick, Berkeley; Gail L. Wong, Oakland; Paul G. Polakis, San Francisco; Bonnee Rubinfeld, Danville, all of Calif.

[73] Assignee: Chiron Corporation, Emeryville, Calif.

[21] Appl. No.: 380,206

[22] Filed: Jan. 30, 1995

Related U.S. Application Data

[63] Continuation of Ser. No. 138,880, Oct. 18, 1993, abandoned, which is a continuation of Ser. No. 776,878, Oct. 16, 1991, abandoned, which is a continuation of Ser. No. 396,910, Aug. 21, 1989, abandoned, which is a continuation-in-part of Ser. No. 260,807, Oct. 21, 1988, abandoned, which is a continuation-in-part of Ser. No. 230,761, Aug. 10, 1988, abandoned.

[51] Int. Cl.$^6$ ............................................. C07K 7/04
[52] U.S. Cl. ............................................. 530/326; 530/350
[58] Field of Search ....................... 435/7.1; 530/326, 530/324, 350

[56] References Cited

U.S. PATENT DOCUMENTS

| | | | |
|---|---|---|---|
| 4,518,584 | 5/1985 | Mark et al. | 424/85 |
| 4,542,092 | 9/1985 | Toya et al. | 430/510 |
| 4,588,585 | 5/1986 | Mark et al. | 424/85 |
| 4,683,195 | 7/1987 | Mullis et al. | 435/6 |
| 4,683,202 | 7/1987 | Mullis | 435/91 |
| 4,699,877 | 10/1987 | Cline et al. | 435/6 |
| 4,745,051 | 5/1988 | Smith et al. | 435/68 |
| 4,762,706 | 8/1988 | McCormick et al. | 424/85 |
| 4,800,159 | 1/1989 | Mullis et al. | 435/172.3 |
| 4,889,818 | 12/1989 | Gelfand et al. | 435/194 |
| 4,965,188 | 10/1990 | Mullis et al. | 435/6 |
| 5,024,947 | 6/1991 | Inlow et al. | 435/240.31 |
| 5,066,584 | 11/1991 | Gyllensten et al. | 435/91 |
| 5,104,975 | 4/1992 | McCormick et al. | 530/350 |
| 5,234,839 | 8/1993 | McCormick et al. | 436/501 |
| 5,372,943 | 12/1994 | Inlow et al. | 435/240.31 |

FOREIGN PATENT DOCUMENTS

| | | |
|---|---|---|
| 0 108 564 A1 | 5/1984 | European Pat. Off. |
| 0 127 839 A2 | 12/1984 | European Pat. Off. |
| 0 258 017 A2 | 3/1988 | European Pat. Off. |
| 0 649 908 A1 | 4/1995 | European Pat. Off. |
| WO 84/01389 | 4/1984 | WIPO |
| WO 85/00974 | 3/1985 | WIPO |
| WO 89/01029 | 2/1989 | WIPO |
| WO 89/01027 | 2/1989 | WIPO |

OTHER PUBLICATIONS

Vogel et al. "Cloning of Bovine GAP and its interaction with Oncogenic ras p. 21", Nature, vol. 335, 1 Sep. 1988, pp. 90–93.
Trahey et al. (1987) Science, vol. 238, pp. 542–545.
Adari et al. (1988) Science, vol. 240, pp. 518–521.
Gibbs et al. (1988) Proc. Nat'l. Acad Sci (USA), vol. 85, pp. 5026–5030.
Clark et al. (1985) Proc. Nat'l. Acad Sci (USA) vol. 82, pp. 5280–5284.
Feramisco et al. (1985) Nature, vol. 314, pp. 639–642.
Aviv et al., "Purification of Biologically Active Globin Messenger RNA by Chromatography on Oligothymidylic acid–Cellulose," Proc. Natl. Acad. Sci., USA, 69:1408–1412 (Jun., 1972).
Barbacid, M., "ras GENES," Ann. Rev. Biochem., 56:779–827 (1987).
Barbacid, M., "Human Oncogenes," In Important Advances in Oncology, DeVita, B., Helman, S., Rosenberg, S., (Eds.), J. P. Lippincott & Co., Philadelphia, PA, pp. 3–22 (1986).
Bos et al, "Amino–acid Substitutions at Codon 13 of the N–ras Oncogene in Human Acute Myeloid Leukaemia," Nature, 315:726–730 (1985).
Burand et al., "Transfection with Baculovirus DNA," Virology, 101:286–290 (1980).
Burnette, "'Western Blotting': Electrophoretic Transfer of Proteins from Sodium Dodecyl Sulfate– Polyacrylamide Gels to Unmodified Nitrocellulose and Radiographic Detection with Antibody and Radioiodinated Protein A," Anal. Biochem., 112:195–203 (1981).
Cales et al., "The Cytoplasmic Protein GAP Is Implicated As The Target For Regulation By the ras Gene Product," Nature, 332:548–551 (Apr. 7, 1988).
Carstens et al., "Infectious DNA from Autographa Californica Nuclear Polyhedrosis Virus," Virology, 101:311–314 (1980).
Chang et al., "Tumorigenic Transformation of Mammalian Cells Induced by a Normal Human Gene Homologous to the Oncogene of Harvey Murine Sarcoma Virus," Nature, 297:479–483 (Jun. 10, 1982).
Cohen, "Nonchromosomal Antibiotic Resistance in Bacteria: Genetic Transformation of Escherichia coli by R–factor DNA," Proc. Natl. Acad. Sci., USA, 69:2110–2114 (Aug. 1972).
Graham et al., "A New Technique for the Assay of Infectivity of Human Adenovirus 5 DNA," Virology, 52:456–467 (1973).
Hunkapiller et al., "Isolation of Microgram Quantities of Proteins from Polyacrylamide Gels for Amino Acid Sequence Analysis," Meth. Enzymol., 91:227–236 (1983).
Hunkapiller et al., "High–Sensitivity Sequencing With A Gas–Phase Sequenator," Meth. Enzymol., 91:399–413 (1983).
Huynh et al, "Constructing and Screening cDNA Libraries in λgt10 and λgt11," In DNA Cloning Techniques: A Practical Approach, D. Glover, (Ed.), IRL Press, Oxford, pp. 49–78 (1985).

(List continued on next page.)

Primary Examiner—David Guzo
Attorney, Agent, or Firm—David A. Gass; Philip L. McGarrigle, Jr.; Robert P. Blackburn

[57] ABSTRACT

Peptides, that inhibit GAP stimulated ras p21 hydrolysis of GTP; peptides that mediate dissociation of GDP from ras p21–GTP complex; and antibodies to the peptides are described. These peptides are useful as cancer diagnostics and therapeutics, particularly to detect cancer cells with an over expression of normal or oncogenic ras p21 protein and to treat cancer caused by ras oncogene. Methods for assaying products of oncogenes using the described peptides and antibodies are also disclosed. Method for treating cancer caused by ras oncogenes is also disclosed.

17 Claims, 20 Drawing Sheets

OTHER PUBLICATIONS

Ish–Horowicz et al., "Rapid and Efficient Cosmid Cloning," *Nucl. Acids Res.*, 9:2989–2998 (1981).

Laemmli, "Cleavage of Structural Proteins during the Assembly of the Head of Bacteriophage T4," *Nature*, 227:680–685 (Aug., 1970).

Lane, "Activation of Related Transforming Genes in Mouse and Human Mammary Carcinomas," *Proc. Natl. Acad. Sci., USA*, 78:5185–5189 (1981).

Lowry et al., "Protein Measurement With the Folin Phenol Reagent," *J. Biol. Chem.*, 193:265–275 (1951).

Luckow et al., "Trends in the Development of Baculovirus Expression Vectors," *Bio./Technology*, 6:47–55 (Jan., 1988).

Maiorella et al., "Large–Scale Insect Cell–Culture For Recombinant Protein Production," *Bio/Technology*, 6:1406–1410 (1988).

Mateucci et al, "Synthesis of Deoxyoligonucleotides on a Polymer Support," *J. Am. Chem. Soc.*, 103:3185–3191 (1981).

Maxam et al, "Sequencing End–Labeled DNA with Base–Specific Chemical Cleavages," *Meth. Enzymol.*, 65:499–560 (1980).

McCormick et al, "Interaction of ras p21 Proteins with GTPase Activating Protein," *Cold Spring Harbor Symp. Quant. Biol.*, 53:849–854 (1988).

Mes–Masson et al., "Overlapping CDNA Clones Define the Complete Coding Region for the P210$^{c-abl}$ Gene Product Associated with Chronic Myelogenous Leukemia Cells Containing the Philadelphia Chromosome," *Proc. Natl. Acad. Sci.*, 83:9768–9772 (1986).

Messing, "New M13 Vectors for Cloning," *Meth. Enzymol.*, 101:20–78 (1983).

Messing et al., "A System for Shotgun DNA Sequencing," *Nucl. Acids Res.*, 9:309–321 (1981).

Mulcahy et al., "Requirement for ras Proto–oncogene Function During Serum–stimulated Growth of NIH 3T3 Cells," *Nature*, 313:241–243 (1985).

Mumby et al., "Chromatographic Resolution and Immunologic Identification of the $\alpha_{40}$ and $\alpha_{41}$ Subunits of Guanine Nucleotide–binding Regulatory Proteins from Bovine Brain," *J. Biol. Chem.*, 263:2020–2026 (Feb. 5, 1988).

Myers et al., "Detection of Single Base Substitutions in Total Genomic DNA," *Nature*, 313:495–498 (1985).

Myers et al., "Detection of Single Base Substitutions by Ribonuclease Cleavage at Mismatches in RNA:DNA Duplexes," *Science*, 230:1242–1246 (1985).

Okayama et al., "A cDNA Cloning Vector That Permits Expression of cDNA Inserts in Mammalian Cells," *Mol. Cell. Biol.*, 3:280–289 (Feb., 1983).

Pizon et al., "Human cDNAs rap1 and rap2 Homologous to the Drosophila Gene Dras3 Encode Proteins Closely Related to ras in the 'Effector' Region," *Oncogene*, 3:201–204 (1988).

Polakis et al., "The Formylpeptide Chemoattractant Receptor Copurifies with a GTP–binding Protein Containing a Distinct 40–kDa Pertussis Toxin Substrate," *J. Biol. Chem.*, 263:4969–4976 (1988).

Pulciani et al., "ras Gene Amplification and Malignant Transformation," *Mol. Cell. Biol.*, 5:2836–2841 (Oct., 1985).

Regnier, F., "High–Performance Liquid Chromatography of Proteins," *Meth. Enzymol.*, 91:137–190 (1983).

Sanger et al., "DNA Sequencing With Chain–terminating Inhibitors," *Proc. Natl. Acad. Sci., USA*, 74:5463–5467 (Dec., 1977).

Schägger et al., "Tricine–Sodium Dodecyl Sulfate–Polyacrylamide Gel Electrophoresis For The Separation Of Proteins In The Range From 1 To 100 kDa," *Anal. Biochem.*, 166:368–379 (1987).

Shaltiel, "Hydrophobic Chromatography," *Meth. Enzymol.*, 104:69–96 (1984).

Shilo et al., "Unique Transforming Gene In Carcinogen–Transformed Mouse Cells," *Nature*, 289:607–609 (1981).

Slamon et al., "Human Breast Cancer: Correlation of Relapse and Survival with Amplification of the HER–2/neu Oncogene," *Science*, 235:177–182 (1987).

Smith et al., "Production of Human Beta Interferon In Insect Cells Infected With A Baculovirus Expression Vector," *Mol. Cell. Biol.*, 3:2156–2165 (1983).

Southern, E., "Detection of Specific Sequences Among DNA Fragments Separated by Gel Electrophoresis," *J. Mol. Biol.*, 98:503–517 (1975).

Summers et al., "A Manual of Methods for Baculovirus Vectors and Insect Cell Culture Procedures," *Texas Agricultural Experiment Station, Bulletin No. 1555*, pp. 1–56 (May, 1987).

Takai et al., "Multiple Small Molecular Weight GTP–Binding Proteins in Bovine Brain Membranes," *In Progress in Endocrinology*, H. Imura et al., (Eds.), Elsevier Science Publishers, B.V., Amsterdam, vol. 2, pp. 995–1000 (1988).

Tamura et al., "Antibodies Against Synthetic Peptides As A Tool For Functional Analysis Of The Transforming Protein pp60$^{src}$," *Cell*, 34:587–596 (1983).

Temeles et al., "Yeast and Mammalian ras Proteins Have Conserved Biochemical Properties," *Nature*, 313:700–703 (Feb., 1985).

Tjian et al., "Catalytic Properties of the SV40 Large T Antigen," *Cold Spring Harbor Symp. Quant. Biol.*, 44:103–111 (1980).

Trahey et al., "Biochemical and Biological Properties of the Human N–ras p21 Protein," *Mol. Cell. Biol.*, 7:541–544 (1987).

Valenzuela et al., "Four Human Carcinoma Cell Lines With Novel Mutations In Position 12 of c–K–ras Oncogene," *Nucl. Acids Res.*, 14:843–852 (1986).

Valeriote et al., "Proliferation–Dependent Cytotoxicity Of Anticancer Agents: A Review," *Cancer Res.*, 35:2619–2630 (1975).

Varmus, H., "The Molecular Genetics of Cellular Oncogenes," *Ann. Rev. Genetics*, 18:553–612 (1984).

Vieira et al., "The pUC Plasmids, an M13mp7–derived System for Insertion Mutagenesis and Sequencing with Synthetic Universal Primers," *Gene*, 19:259–268 (1982).

Waldo et al., "Identification and Purification From Bovine Brain of a Guanine–nucleotide–binding Protein Distinct From $G_s$, $G_i$ and $G_o$," *Biochem. J.*, 246:431–439 (1987).

Wilchek et al., "Affinity Chromatography," *Meth. Enzymol.*, 104:3–55 (1984).

Willumsen et al., "Mutational Analysis of a ras Catalytic Domain," *Mol. Cell. Biol.*, 6:2646–2654 (1986).

Winter et al., "A Method To Detect And Characterize Point Mutations In Transcribed Genes: Amplification And Overexpression Of The Mutant c–Ki–ras Allele In Human Tumor Cells," *Proc. Natl. Acad. Sci., USA*, 82:7575–7579 (1985).

Wong et al., "Detection of Activated $M_R$ 21,000 Protein, the Product of ras Oncogenes, Using Antibodies with Specificity for Amino Acid 12," *Cancer Res.*, 46:6029–6033 (1986).

Yokota et al., "Alterations of myc, myb, and ras$^{Ha}$ Proto-oncogenes in Cancers are Frequent and Show Clinical Correlation," *Science*, 231:261–265 (Jan., 1986).

Borregaard et al., "Subcellular Localization of the b–Cytochrome Component of the Human Neutrophil Microbicidal Oxidase:Translocation during Activation," *J. Cell Biol.*, 97:52–61 (Jul., 1983).

Clonetech Laboratories, Inc., *Human Placenta DNA Library*, pp. 11, 41–43.

DeClue et al., "A Conserved Domain Regulates Interactions of the v–fps Protein–Tyrosine Kinase With the host Cell," *Proc. Nat'l Acad. Sci., USA*, 84:9064–9068 (Dec., 1987).

Devlin et al., "Novel Expression of Chimeric Plasminogen Activators in insect Cells," *Bio/Technology*, 7:286–292 (Mar., 1989).

Duanmu et al., "Tubulin–dependent Hydrolysis of Guanosine Triphosphate as a Screening Test to Identify New Antitubulin Compounds With Potential as Antimitotic Agents:Application to Carbamates," *Cancer Research*, 49:1344–1348 (Mar. 15, 1989).

Escobedo et al., "Role of Tyrosine Kinase and Membrane–Spanning Domains in Signal Transduction by the Platelet–Derived Growth Factor Receptor," *Mol. and Cell. Biol.*, 8(12):5126–5131 (Dec., 1988).

Grand et al., "Purification and Characterization of the Protein Encoded by the Activated Human N–ras Gene and Its Membrane Localisation," *Oncogene*, 1:305–314 (1987).

Hall et al., "Analysis of Mammalian Ras Effector Function," *Cold Spring Harbor Laboratory, Cold Spring Harbor Press*, p. 85 (1988) (Abstract).

Higashijima et al., "Mastoparan, a Peptide Toxin from Wasp Venom, Mimics Receptors by Activating GTP–binding Regulatory Protein (G Proteins)," *J. of Biol. Chem.*, 263(14):6491–6494 (May 15, 1988).

Higuchi et al., "A General Method of In Vitro Preparation and Specific Mutagenesis of DNA Fragments: Study of Protein and DNA Interactions," *Nucleic Acids Res.*, 16(15):7351–7367 (1988).

Ho et al., "Site–directed Mutagenesis by Overlap Extension Using the Polymerase Chain Reaction," *Gene*, 77:51–59 (1989).

Hopp et al., "A Short Polypeptide Marker Sequence Useful For Recombinant Protein Identification and Purification," *Bio/Technology*, 6:1204–1210 (Oct., 1988).

Jacobs et al., "Isolation and Characterization of Genomic and cDNA Clones of Human Erythropoietin," *Nature*, 313:806–810 (Feb. 28, 1985).

Köhler and Milstein, "Continuous Cultures of Fused Cells Secreting Antibody of Predefined Specificity," *Nature*, 256:495–497 (Aug. 7, 1975).

Lacal et al., "Expression of Normal and Transforming H–ras genes in *Escherichia coli* and Purification of Their Encoded p21 Proteins," *Proc. Nat'l Acad. Sci., USA*, 81:5305–5309 (Sep., 1984).

Lathe, R., "Synthetic Oligonucleotide Probes Deduced From Amino Acid Sequence Data Theoretical and Practical Considerations," *J. Mol. Biol.*, 183:1–12 (1985).

Luckow and Summers, "High Level Expression of Nonfused Foreign Genes with *Autographa californica* Nuclear Polyhedrosis Virus Expression Vectors," *Virology*, 170:31–39 (1989).

Maniatis et al., *Molecular Cloning: A Laboratory Manual*, Cold Spring Harbor Laboratory, Cold Spring Harbor Press, pp. 254–255 (1982).

Manne et al., "Guanosine Nucleotide Binding by Highly Purified Ha–ras–encoded p21 Protein Produced in *Escherichia coli*," *Proc. Nat'l Acad. Sci., USA*, 81:6953–6957 (Nov., 1984).

Marshall et al., "A C–terminal Domain of GAP is Sufficient to Stimulate ras p21 GTPase Activity," *EMBO J.*, 8(4):1105–1110 (1989).

McCormick et al., "GTPase Activating Protein (GAP) May Be The Ras Effector," *Cold Spring Harbor Laboratory, Cold Spring Harbor Press*, p. 84 (1988).

McCormick, F., "ras GTPase Activating Protein: Signal Transmitter and Signal Terminator," *Cell*, 56:5–8 (Jan. 13, 1989).

Merrifield, B., "Solid Phase Synthesis," Bioscience Reports, 5:353–376 (1985).

Merrifield, B., "Solid Phase Synthesis," *Science*, 232(4748):341–347 (Apr. 18, 1986).

*New England BioLabs Catalog 1986/87*, New England BioLabs, Inc., MA, USA, pp. 60–62 (1986–1987).

Papageorge et al., "Comparative Biochemical Properties of p21 ras Molecules Coded for by Viral and Cellular ras Genes," *Journal of Virology*, 44(2):509–519 (Nov., 1982).

Pendergast et al., "Baculovirus Expression of Functional P210 BCR–ABL Oncogene Product," *Oncogene*, 4:759–766 (1989).

Record et al., "A Rapid Isolation Procedure of Plasma Membranes From Human Neutrophils Using Self–Generating Percoll Gradients. Importance of pH in Avoiding Contamination by Intracellular Membranes," *Biochim. et Biophys. Acta.*, 89:1–9 (1985).

Rey et al., "Antibodies to Synthetic Peptide from the Residue 33 to 42 Domain of c–Ha–ras p21 Block Reconstitution of the Protein With Different Effectors," *Mol. Cell. Biol.*, 9(9):3904–3910 (Sep., 1989).

Sadowski et al., "A Noncatalytic Domain Conserved among Cytoplasmic Protein–Tyrosine Kinases Modifies the Kinase Function and Transforming Activity of Fujinami Sarcoma Virus P130$^{gag-fps}$," *Mol. and Cell. Biol.*, 6(12):4396–4408 (Dec., 1986).

Sadowski and Pawson, "Catalytic and Non–catalytic Domains of the Fujinami Sarcoma Virus P130$^{gag-fps}$ Protein–tyrosine Kinase Distinguished by the Expression of v–fps Polypeptides in *Escherichia coli*," *Oncogene*, 1:181–191 (1987).

Saiki et al., "Primer–Directed Enzymatic Amplification of DNA with a Thermostable DNA Polymerase," *Science*, 239–487–491 (Jan. 29, 1988).

Sambrook et al., *Molecular Cloning A Laboratory Manual, Second Edition*, Cold Spring Harbor Laboratory, Cold Spring Harbor Press, 11.7–11.8, 11.45–11.49,11.55–11.57, (1989).

Schaber et al., "Ras Interaction with the GTPase–Activating Protein (GAP)," *Proteins:Structure, Function, and Genetics*, 6(3):306–315 (1989).

Shacter, E., "Organic Extraction of P$_i$ with Isobutanol/Toluene," *Anal. Biochem.*, 138:416–420 (1984).

Shadle et al., "Human Macrophage Colony–Stimulating Factor Heterogeneity Results From Alternative mRNA Splicing, Differential Glycosylation, and Proteolytic Processing," *J. Cell. Biochem.*, 40:91–107 (1989).

Sigal et al., "Identification of Effector Residues and a Neutralizing Epitope of Ha–ras–Encoded p21," *Proc. Nat'l Acad. Sci., USA*, 83(13):4725–4729 (Jun., 1986).

Sigal, I.S., "The ras Oncogene: A Structure and Some Function," *Nature*, 332:485–486 (Apr. 7, 1988).

Suggs et al., "Use of Synthetic Oligonucleotides As Hybridization Probes: Isolation of Cloned cDNA Sequences for Human β2–Microglobulin," *Proc. Nat'l Acad. Sci., USA*, 78(11):6613–6617 (1981).

Tamaoki et al., "Expression of Intact K1–ras p21 Protein in *Escherichia coli*," *Biochem. Biophys. Res. Comm.*, 132(1):126–133 (Oct. 15, 1985).

Trahey and McCormick, "Control of Ras p21 Function In Vivo By Guanine Nucleotides," Meeting on Oncogenes, NCI, p. 257 (Jul., 1987).

Trahey et al., "Molecular Cloning of Two Types of GAP Complementary DNA From Human Placenta," *Science*, 242:1697–1700 (Dec. 23, 1988).

Ueda et al., "GTPase Activating Proteins From the smg–21 GTP–binding Protein Having the Same Effector Domain as the Ras Proteins in Human Platelets," *Biochem. Biophys Res. Commun.*, 159(3):1411–1419 (Mar. 31, 1989).

Wang and Parsons, "Deletions and Insertions within an Amino–Terminal Domain of pp60$^{v-src}$ Inactivate Transforation and Modulate Membrane Stability," *J. Virology*, 63(1):291–302 (Jan., 1989).

Weaver et al., Genetics, Wm. C. Brown Publishers, Dubuque, Iowa, pp. 451–457 (1989).

Wells et al., "An Improved Method for Purifying 2',5'–Oligoadenylate Synthetases," *J. Biol. Chem.*, 259(2):1363–1370 (Jan. 25, 1984).

Wendler and Boschelli, "Src Homology 2 Domain Deletion Mutants of p60$^{v-src}$ Do Not Phosphorylate Cellular Proteins of 120–150 kDa," *Oncogene*, 4(2):231–236 (Feb., 1989).

Gilboa, E., "Retrovirus Vectors and Their Uses in Molecular Biology," *BioEssays*, 5(6):252–257 (1986).

Mullis and Faloona, "Specific Synthesis of DNA in Vitro via a Polymerase–Catalyzed Chain Reaction," *Methods in Enzymology*, 155:335–350 (1987).

Mullis et al., "Specific Enzymatic Amplification of DNA In Vitro: The Polymerase Chain Reaction," *Cold Spring Harbor Symposia on Quantitative Biology*, Cold Spring Harbor Laboratory, vol. LI, pp. 263–273, (1986).

Innis et al., (Eds.), PCR Protocols: A Guide To Methods and Applications, Academic Press, Inc., Harcourt Brace Jovanovich, Publishers, San Diego, CA, pp. 4–7 (1990).

REDUCED 10% SDS PAGE
( COOMASSIE-STAINED )

FIG. 3

ILE MET PRO GLU GLU GLU TYR SER GLU PHE LYS

```
ATC ATG CCC GAG CAG GAG TAC TCC GAG TTC AAG
 T       A   AGA  A   T   T   A   T   A
 A       T                A
         G                G
                         AGC
                          T
```

FIG. 4

Ile MET Pro Glu Glu Glu Tyr Ser Glu Phe Lys

GW13 5'ATC ATG CCT GAG CAG GAG TAC TCT GAG TTC AAG'3

GW15 5'ATC ATG CCT GAG CAG GAG TAC AGT GAG TTC AAG'3

GW17 5'ATC ATG CCT GAG GAG GAG TAC TCT GAG TTC AAG'3

GW19 5'ATC ATG CCT GAG GAG GAG TAC AGT GAG TTC AAG'3

FIG. 5A

```
681   ACCATTTTAGGATTATTGCTATGTGTGGAGATTACTACATTGGTGGAAGACGTTTCTTCACTGTCAGACCTAATAGGTTATTACAGTCATGTTTCTG   780
229     H  F  R  I  I  A  M  C  G  D  Y  Y  I  G  G  R  R  F  S  S  L  S  D  L  I  G  Y  Y  S  H  V  S  C    261

781   TTTGCTTAAAGGAGAAATTACTTTACCAGTGCCACCACCAGAGCCAGTAGAAGATAGAAGGCGTGTACGAGCTATTCTACCTTACACAAAAGTACCA   880
262     L  L  K  G  E  K  L  L  Y  P  V  A  P  P  E  P  V  E  D  R  R  R  V  R  A  I  L  P  Y  T  K  V  P    294

881   GACACTGATGAATAAGTTTCTTAAAGGAGATATGTTCATTGTTCATAATGAATTAGAAGATGGATGGGTTACAAATTTAAGAACAGATGAAC      980
295     D  T  D  E  I  S  F  L  K  G  D  M  F  I  V  H  N  E  L  E  D  G  W  M  W  V  T  N  L  R  T  D  E  Q  328

981   AAGGCCTTATTGTTGAAGACCTAGTAGAAGAGGTGGGCCGTAGAGAAGAGGATCCACATGAAGGAAAATCCACATGAAGGAAGATTCCAAACAGGAAGC   1080
329     G  L  I  V  E  D  L  V  E  E  V  G  R  E  E  D  P  H  E  G  K  I  W  F  H  G  K  I  S  K  Q  E  A     361

1081  TTATAATTTACTAATGACAGTTGGTGTCAAGTCTGCAGTTTTCTGTGAGGCCCTCAGATAATACTCCTGGCGATTATTCACTTTATTCCGACCAATGAA  1180
362     Y  N  L  L  M  T  V  G  Q  V  C  S  F  L  V  R  P  S  D  N  T  P  G  D  Y  S  L  Y  F  R  T  N  E    394
                                 A                                                              S

1181  AATATTCAGCGATTTAAAATATGTCCAACAACAATCAGTTTATGATGGAGGCCGGTATTATAACAGCATTGGGGACATCATAGATCACTATCGAA    1280
395     N  I  Q  R  F  K  I  C  P  T  P  N  N  Q  F  M  M  G  G  R  Y  Y  N  S  I  G  D  I  I  D  H  Y  R  K 428

1281  AAGAACAGATTGTTGAAGGATATTATCTTAAGGAACCTGTACCAATGCAGGATCAAGAACTCAATGACACAGTGGATGGCAAGGAAATCTATAA     1380
429     E  Q  I  V  E  G  Y  Y  L  K  E  P  V  P  M  Q  D  Q  E  Q  V  L  N  D  T  V  D  G  K  E  I  Y  N    461
                                                                             A

1381  TACCATCCGTCGTAAAACAAAGGATGATGCCCAACTTATTTATTTTGAAAGCGAAAAACGAGCTACCAAACCAAAGGATTAATAGATCTCAGTGTCT   1480
462     T  I  R  R  K  T  K  D  D  A  Q  L  I  Y  F  E  S  E  K  R  A  T  K  P  K  G  L  I  D  L  S  V  C  S  V  Y 494

1481  TTTATCTTAGAGGGTAGTGATGCCCAACTTATTTATTTTGAAAGCGAAAAACGAGCTACCAAACCAAAGGATTAATAGATCTCAGTGTATGTCTGTCT  1580
495     F  I  L  E  G  S  D  A  Q  L  I  Y  F  E  S  E  K  R  A  T  K  P  K  G  L  I  D  L  S  V  C  S  V  Y    528

1581  ATGTCGTTCATGATAGTCTCTTTGGCAGGCCAAACTGTTTCAGATAGTCAGCACTTTAGTGAAGAACATTACATCTTTACTTTGCAGGAGAAAC    1680
529     V  V  H  D  S  L  F  G  R  P  N  C  F  Q  I  V  V  Q  H  F  S  E  E  H  Y  I  F  Y  F  A  G  E  T    561
```

FIG.5B

```
1681  TCCAGAACAAGCAGAGGATTGGATGAAAGGTCTGCAGGCCATTTGCAATTTACGGAAAAGTAGTCCAGGACACCAATAAACGCCTTCGTCAGGTCAGC  1780
562   P  E  Q  Q  E  D  W  M  K  G  L  Q  A  F  C  N  L  R  K  S  S  P  G  T  S  N  K  R  L  R  Q  V  S  594

1781  AGCCTTGTTTACATATTGAAGAAGCCCATAAACTCCCAGTAACATTTACTAATCCATATATTGTAACATCTACTGGAATAGTGTCCAAGTAGCAAAAA  1880
595   S  L  V  L  H  I  E  E  A  H  K  L  P  V  K  H  F  T  N  P  Y  C  N  I  Y  L  N  S  V  Q  V  A  K  T  628
            I

1881  CTCATCGCAAGGGAAGGGCAAAACCAGTTGTCAGAGAGTTTGTCTTTGATGATCTTCCTCCTGACATCAATAGATTTGAAATAACTCTTAGTAATAA   1980
629   H  A  R  E  G  Q  N  P  V  W  S  E  E  F  V  F  D  D  L  P  P  D  I  N  R  F  E  I  T  L  S  N  K  661

1981  CTCATCGCAAGGGAAGGGCAAAACCAGTTGTCAGAGAGTTTGTCTTTGATGATCTTCCTCCTGACATCAATAGATTTGAAATAACTCTTAGTAATAA   2080
662   H  A  R  E  G  Q  N  P  V  W  S  E  E  F  V  F  D  D  L  P  P  D  I  N  R  F  E  I  T  L  S  N  K  694

2081  CATATACCATTAAAGGTATTGAACCAGGTCCCTGCGTGTTCGAGCACGATACTCTATGGAAAAAATCATGCCAGAAGAGTACAGTGAATTTAAAG    2180
695   H  I  P  L  K  G  I  E  P  G  S  L  R  V  R  A  R  Y  S  M  E  K  I  M  P  E  E  Y  S  E  F  K  E  728

2181  AGCTTATATGCAAAGGAACTTCATGTAGTCGTTATCATACTTCCAGCCATCCTACTGGCCAGCATCCTACTGGCCAGCATCCTACTGGGATTTTCT    2280
729   L  I  L  Q  K  E  L  H  V  V  Y  A  L  S  H  V  C  G  Q  D  R  T  L  L  A  S  I  L  L  R  I  F  L  761
                                                                                          K

2281  TCACGAAAAGTCTGAATCGTTGTTGTTATGCACACTAAATGACAGAGAAATAAGCATGGAAGATGAAGCATCCAACTTGCA                  2380
762   H  E  K  L  E  S  L  L  L  C  T  L  N  D  R  E  I  S  M  E  D  E  A  T  T  L  F  R  A  T  T  L  A  794

2381  AGCCACCTTGATGGAGCAGTATATGAAAGCCACTGCTACACAGTTTGTTCATCATGCTTTGAAAGACTCTATTTTAAAGATAATGGAAAGCAAGCAGTCTT  2480
795   S  T  L  M  E  Q  Y  M  K  A  T  A  T  Q  F  V  H  H  A  L  K  D  S  I  L  K  I  M  E  S  K  Q  S  C  828
               S                                                       R

2481  GTGAGTTAAGTCCATCCAAGTTAGAAAAATGAAGATGTGAACACTAATTTAACACACTTGCAATACTTCAGAGCTTGTGGAGAAATATTCAT       2580
829   E  L  S  P  S  K  L  E  K  N  E  D  V  N  T  N  L  T  H  L  L  N  I  L  S  E  L  V  E  K  I  F  M  861
                                             A

2581  GGCTTCAGAAATACTTCCACCGACATTGAGATATATTTATGGTGTGTTTACAGCTGCAAATCTGTCAGCATAAGTGGCCTACAAATACCACCATGAGAACAAGA  2680
862   A  S  E  I  L  P  P  T  L  R  Y  I  Y  G  C  L  Q  K  S  V  Q  H  K  W  P  T  N  T  T  M  R  T  R  894
```

FIG. 5C

| | | |
|---|---|---|
| 2681 | GTGTTAGTGGTTTGTTTTCTTGACTCATCTGCCATCCTGAATCCACGGATGTTCAATATCATCTCAGATTCTCCATCTCCTATTGCTGCAA | 2780 |
| 895 | V V S G F V F L R L I C P A I L N P R M F N I I S D S P P I A A R | 928 |
| 2781 | GAACACTGATATTAGTGGCTAAATCTGTGCAGAACTTAGCAAATCTTGTGGAGCTAAGGAGCCTACATGGAAGGTGTCAATCCATTCATCAA | 2880 |
| 929 | T L L V A K S V Q N L A N L V E F G A K E P Y M E G V N P F I K | 961 |
| 2881 | AAGCAACAAACATCGTATGATCATGTTTTTAGATGAACTTGGGAATGTACCTGAACTTCCGGACACTACAGAGCATTCCAGTCGAACTGACCTGTCCCGTGAT | 2980 |
| 962 | S N K H R M I M F L D E L G N V P E L P D T T E H S R T D L S R D | 994 |
| 2981 | TTAGCAGCCATTCCATGAGATTTGCGTGGCTCATTCAGATGAACTTCGAACGCTCAGTAATGAGCCTCACAGCAGCTATTGAAAAGCTTCTGG | 3080 |
| 995 | L A A L H E I C V A H S D E L R T L S N E R G A Q Q H V L K K L L A | 1028 |
| 3081 | CTATAACAGAACTGCTTCAACAAAAACAGTATACAAAAACCAATGATGTCAGGTAGCAGCCTTCGCCCCAGTGTCTGCATGATTCAGCATGT | 3180 |
| 1029 | I T E L L Q Q K Q N Q Y T K T N D V R | 1047 |
| 3181 | CCAACATGGTAATTCACTTCAGTTAATGTCTCCTTTGCTCTTGCCAAAAATAGCACACTTTCCACATTCCAGTGATGTGAGCTATGCAAACAAA | 3280 |
| 3281 | TCCAAGATTCTGCTGGTGAATAACTATGCCAGCAACCTTGTAAGCTCACTATCTGTGCAGGATATTTGCACTATTCCACATGTATCTTAACAACCTC | 3380 |
| 3381 | TGACCCTTGGTGTGTACAGACCACCTTCACAAAACGAACTATGACTGTATATCTCGAACTTTCAAATATATTTCAGTACACCCAGTGCC | 3480 |
| 3481 | AAAGTTTTGCTGTCTCTTAGAAGAACTATGACCATTTGACTGTTCAAATGTACAAGTTGTATAACGGATTGCAGACTGTTCTTAC | 3580 |
| 3581 | TGTAACTACTTCCTGATTAGGAATATACTCTGCTATTTCTCTTGCTGCATTTGACTGTTCATGCAGTTGTCATTATAATAGGAACAATCTTTG | 3680 |
| 3681 | CTGTATACTTTAAAAAATACTCTGTCAAATTGTCAAAGACTGTATTAGATCTCATAATGCTTTGTTAAATTCAGTAAATATTATT | 3780 |
| 3781 | TACGACTTATATTTGTTGAAATGCAATGTACCCATTCAACCATTCTTTATGACTACCAATCTACTTATCCATCTTTGACTCTTGACTCTGACTACTGTTGTATCTGCTGATATT | 3880 |
| 3881 | GGTTGTGTATTGATCAATGCATGTACCCCTTTGATTATGCAGACAACCTCAACTTATCACCTGCCTAACTTATCATCAGTTTAAACTAGAATGCTTTGTTAAAGTTATTGTT | 3980 |
| 3981 | CATTATTTGTGCTACCCTTTGATTATGCAGACAACCTCACACTCTCGACTACTGTGTATCTCGGATATT | 4080 |
| 4081 | TACTTCAACGTATAGTTTTATTACTTCTGTATGTGTATTTGTGAAGTATTCACAAGGTTAAGTTAAAATAAACCAAGGATATCTGCAAAAAA | 4180 |
| 4181 | AAAAAA 4187 | |

```
 681  ACCATTTTAGGATTATTGCTATGTGTGGAGATTACTACATTGTGGAAGACGTTTTCTTCACTGTCAGACCTAATAGGTTATTACAGTCATGTTTCTTG    780
 229    H  F  R  I  I  A  M  C  G  D  Y  Y  Y  I  G  G  R  R  F  S  S  L  S  D  L  I  G  Y  Y  S  H  V  S  C       261

781  TTTGCTTAAAGGAGAAAAATTACTTTACCCAGTTGCCACCACCAGAGCCAGTAGAAGATAGAAGGGTGTACGAGCTATTCTACCTTACACAAAGTACCA    880
 262    L  L  K  G  E  K  L  L  Y  P  V  A  P  P  E  P  V  E  D  R  R  R  V  R  A  I  L  P  Y  T  K  V  P       294

881  GACACTGATGAAATAAGTTTCTTAAAAGGAGATATGTTCATTGTTCATAATGAATTAGAAGATGGATGGGTTACAAATTTAAGAACAGATGAAC        980
 295    D  T  D  E  I  S  F  L  K  G  D  M  F  I  V  H  N  E  L  E  D  G  W  M  W  V  T  N  L  R  T  D  E  Q       328

981  AAGGCCTTATTGTTGAAGACCTAGTAGAAGAGGTGGGCCGGGAAGAAGATCCACATGAAGGGAAAAATATGGTTCATGGAAGATTTCAAACAGGAAGC    1080
 329    G  L  I  V  E  D  L  V  E  E  V  G  R  E  E  D  P  H  E  G  K  I  W  F  H  G  K  I  S  K  Q  E  A       361

1081  TTATAATTTACTAATGACAGTTGGTCAAGTCTGCAGTTTTCTTGTGAGGCCCTCAGATAATACTCCTGGCGATTATTCACTTTATTCCGGACCAATGAA    1180
 362    Y  N  L  L  M  T  V  G  Q  [V]  C  S  F  L  V  R  P  S  D  N  T  P  G  D  Y  S  L  Y  F  R  T  [N]  E       394
                                  [A]                                                                  [S]

1181  AATATTCAGGCGATTTAAAATATGTCCAACGCCCAAACAATCAGTTTATGATGGAGGCCGGTATTATAACAGCATTGGGGACATCATAGATCACTATGAA    1280
 395    N  I  Q  R  F  K  I  C  P  T  P  N  N  Q  F  M  M  G  G  R  Y  Y  N  S  I  G  D  I  D  H  Y  R  K       428

1281  AAGAACAGATTGTTGAAGGATATATCTTAAGGAACCTGTTAAGGAGTATCAAGAACAGTGGATGCAATGACAGTGGATGGCAAGGAAATCTATAA    1380
 429    E  Q  I  V  E  G  Y  Y  L  K  E  P  V  P  M  Q  D  Q  E  Q  V  L  N  D  [T]  V  D  G  K  E  I  Y  N       461
                                                                                 [A]

1381  TACCATCCGTCTAAAACAAAGGATGCCTTTTATAAAAACATTGTTAAGAAAGGTTATCTCTGAAAAGGGCAAAGAGAAAACGTTGAAAATTTATAT    1480
 462    T  I  R  R  K  T  K  D  A  F  Y  K  N  I  V  K  K  G  Y  L  L  K  K  G  K  R  W  K  N  L  Y       494

1481  TTTATCTTAGAGGGTAGTGATGCCCAACTTATCTATTTTGAAAGCGAAAAACGAGCTACCAAACCAAAGGATTAATAGATCTCAGTGTATGTTCTGTCT    1580
 495    F  I  L  E  G  S  D  A  Q  L  I  Y  F  E  S  E  K  R  A  T  K  P  K  G  L  I  D  L  S  V  C  S  V  Y       528

1581  ATGTCGTTCATGATAGTCTCTTTGGCAGGCCAAACTGTTTCAGATAGTTCAGCCACTTTAGTGAAGAACATTACATCTTTACTTGCAGGAGAAAC    1680
 529    V  V  H  D  S  L  F  G  R  P  N  C  F  Q  I  V  V  Q  H  F  S  E  E  H  Y  I  F  Y  F  A  G  E  T       561
```

| Peptide | Position |
|---|---|
| G65 | 876-890 |
| G73 | 975-990 |
| cGAP 13 | 890-906 |
| Peptide 891 | 891-906 |

FIG. 11

AMINO ACID ANALYSIS OF cGAP 13

| Sample Number: A | | | Sample Number: B | | |
|---|---|---|---|---|---|
| Sample Weight: 0.584 mg | | | Sample Weight: 0.838 mg | | |
| Expected Amino Acid Residues: | | | Expected Amino Acid Residues: | | |
| Asp | | | Asp | | |
| Thre | 2 | 1.8 | Thre | 2 | 1.8 |
| Ser | 1 | 1.1 | Ser | 1 | 1.1 |
| Glu | | | Glu | | |
| Pro | | | Pro | | |
| Gly | 1 | 1.1 | Gly | 1 | 1.2 |
| Ala | | | Ala | | |
| Val | 3 | 2.9 | Val | 3 | 3.0 |
| Met | 1 | 0.9 | Met | 1 | 0.9 |
| Ileu | 1 | 0.9 | Ileu | 1 | 0.8 |
| Leu | 2 | 2.2 | Leu | 2 | 2.2 |
| Tyr | | | Tyr | | |
| Phe | 2 | 2.0 | Phe | 2 | 2.1 |
| His | | | His | | |
| Lys | | | Lys | | |
| Arg | 3 | 3.1 | Arg | 3 | 2.8 |
| Cys | 1 | 0.9 | Cys | 1 | 1.1 |
| Trp | | | Trp | | |
| Gln | | | Gln | | |
| Asn | | | Asn | | |
| Total: 17 | | | Total: 17 | | |

GTPASE ACTIVATING PROTEIN FRAGMENTS

This application is a continuation of application Ser. No. 08/138,880, filed Oct. 18, 1993, now abandoned, which is a continuation of Ser. No. 07/776,878, filed Oct. 16, 1991, now abandoned, which is a continuation of Ser. No. 07/396,910, filed Aug. 21, 1989, now abandoned, which is a continuation in part of Ser. No. 07/260,807, filed Oct. 21, 1988, now abandoned, which is a continuation in part of Ser. No. 07/230,761, filed Aug. 10, 1988, now abandoned.

FIELD OF THE INVENTION

This invention relates generally to the field of oncology, and particularly to compositions useful in diagnostic testing and therapy for cancer. More specifically, the invention concerns peptide sequences, compositions containing the same, and methods for using the same as cancer diagnostics and therapeutics.

BACKGROUND OF THE INVENTION

Several genes have been identified that are thought to play a role in regulating normal cell growth. A subset of these genes, termed ras, consists of at least three members, N-ras, H-ras, and K-ras2. Altered forms of ras, termed oncogenes, have been implicated as causative agents in cancer. Both the normal cellular genes and the oncogenes encode chemically related proteins, generically referred to as ras p21 protein.

Ras oncogenes, and their normal cellular counterparts, have been cloned and sequenced from a variety of species. Comparison of the structure of these two genes has revealed that they differ by point mutations that alter the amino acid sequence of the ras p21 protein. Naturally occurring mutations in the ras oncogenes have been identified in codons 12, 13, 59, and 61. In vitro mutagenesis work has shown that mutations in codon 63, 116, 117 and 119 also result in transforming activity. The most frequently observed mutation which converts a normal cellular ras gene into its oncogenic counterpart is a substitution of glycine at position 12 by any other amino acid residue, with the exception of proline. Transforming activity is also observed if glycine is deleted, or if amino acids are inserted between alanine at position 11 and glycine at position 12.

Mutations at position 61 also play an important role in the generation of ras p21 protein oncogenes. Substitution of glutamine by any other amino acid, except proline or glutamic acid in the cellular ras gene yields ras oncogenes with transforming activity.

In relation to normal cellular ras genes and their oncogenic counterparts, there are at least four known retroviral ras oncogenes which exhibit transforming activity. Unlike their non-retroviral analogues, the retroviral genes exhibit two mutations. The biological significance of these double mutations is at present unclear.

Both the normal ras p21 and oncogenic ras p21 proteins, regardless of their phylogenetic origin, bind guanine nucleotides, GTP and GDP, and possess intrinsic GTPase activity. See Temeles et al., 1985 *Nature*, 313:700. The significance of these biochemical properties to the biological activities of the ras p21 proteins has been demonstrated as follows: first, microinjection of anti-ras p21 antibodies that interfere with guanine nucleotide binding reverses the malignant phenotype of NIH 3T3 cells transformed by ras oncogenes. See Clark et al., 1985 *Proc. Natl. Acad. Sci. U.S.A.*, 82:5280 and Feramisco et al., 1985 *Nature*, 314:639. Second, ras oncogenic proteins that exhibit mutations which result in the inability of p21 to bind guanine nucleotides do not transform NIH 3T3 cells. Willumsen et al., 1986 *Mol. Cell. Biol.*, 6:2646. Third, some ras oncogenes produce p21 proteins that have much reduced GTPase activity compared to their normal cellular counterparts.

Recently a cytoplasmic factor has been identified which stimulates normal ras p21 GTPase activity, but does not affect GTPase activity associated with the oncogenic mutants. See M. Trahey and F. McCormick, 1987 *Science*, 238:542. The activity has been associated with a protein, termed GAP, which is the acronym for GTPase activating protein. GAP is thought to be a cytoplasmic protein but is presumably capable of moving from the cytosol to the plasma membrane where it interacts with p21.

As alluded to above, ras oncogenes have been implicated in the development of a variety of tumors, and have been shown to be involved in about 10–40% of the most common forms of human cancer. See H. Varmus, 1984 *Annual Rev. Genetics*, 18:553 and M. Barbacid, 1986, in *Important Advances in Oncology*, ed. B. DeVita, S. Helman, S. Rosenberg, pages 3–22, Philadelphia:Lippincott. For example, ras oncogenes have been consistently identified in carcinomas of the bladder, colon, kidney, liver, lung, ovary, pancreas and stomach. They also have been identified in hematopoietic tumors of lymphoid and myeloid lineage, as well as in tumors of mesenchymal origin. Furthermore, melanomas, teratocarcinomas, neuroblastomas, and gliomas have also been shown to possess ras oncogenes.

Considering the possible association of ras oncogenes and cancer, there has been considerable work focused on diagnostic tests for detecting the presence of the oncogene product, p21, or the mutant oncogenes. Early tests, which are still employed in many instances, identify the presence of ras oncogenes in transfection assays which identify p21 by its ability to transform NIH 3T3 cells. See Lane et al., 1981, *Proc. Natl. Acad. Sci. USA*, 78:5185 and B. Shilo, and R. A. Weinberg, 1981, *Nature*, 289:607. This method is insensitive, laborious, and to be performed adequately, requires a skilled laboratory technician.

A second diagnostic method centers around oligonucleotide probes to identify single, point mutations in genomic DNA. This technique is based on the observation that hybrids between oligonucleotides form a perfect match with genomic sequences, that is, non-mutated genomic sequences are more stable than those that contain a single mismatch. An example of the latter is a point mutation in p21 associated with the ras oncogenes. Although this technique is clearly more sensitive and easier to perform than the transfection assay, it is nevertheless also cumbersome to perform. This is because there are theoretically almost 100 base substitutions which can yield ras oncogenes. Thus, in order to be able to detect these substitutions, multiple oligonucleotide probes must be employed containing each of the three possible substitutions at a particular residue. See Bos et al., 1985, *Nature*, 315:726 and Valenzuela et al., 1986, *Nuc. Acid Res.*, 14:843.

In addition to the transfection and oligonucleotide assays, additional nucleic acid hybridization techniques have been developed to identify ras oncogenes. One such method is based on the unusual electrophoretic migration of DNA heteroduplexes containing single based mismatches in denaturing gradient gels. See Myers et al., 1985, *Nature*, 313:495. This technique only detects between about 25–40% of all possible base substitutions, and requires a skilled technician to prepare the denaturing gradient gels. More sensitive techniques which are refinements of this technique are described by Winter et al., 1985, *Proc. Natl. Acad. Sci. USA*, 82:7575 and Myers et al., 1985, *Science*, 230:1242.

Immunologic approaches have been taken to detect the product of the ras oncogenes. Polyclonal or monoclonal antibodies have been generated against the intact ras oncogene p21, or against chemically synthesized peptides having sequences similar to oncogene p21, or the non-transforming counterpart. See U.S. patent application Ser. No. 938,598 (now abandoned); EP Patent Publication 108,564 to Cline et al; Tamura et al., 1983, Cell, 34:587; PCT Application WO/84/01389 to Weinberg et al. For the most part antibodies have been disappointing as diagnostic tools with which to identify ras oncogenic p21 in human tissue sections. This is because either the antibodies that have been generated to date recognize the normal cellular ras p21 protein as well as the oncogenic protein, or, in those instances in which a monoclonal antibody has been generated that specifically recognizes the oncogenic protein, non-specific staining of tumor biopsies is still observed.

While ras oncogenic p21 is an effective tumorigenic agent, recent studies have shown that normal ras p21 can induce the malignant phenotype. See Chang et al., 1982, *Nature*, 297:7479 and Pulciani et al., 1985, *Mol. Cell. Biol.*, 5:2836. For example, transfection of normal H-ras DNA has been shown to induce malignant transformation. It is further noteworthy that normal ras gene amplification has been observed in several human tumors, and has an apparent incidence of about 1%. Pulciani, et al., above; Yokota et al, 1986, *Science*, 231:261. The various diagnostic tests used to detect ras oncogenes or oncogenic p21 have been applied to the detection of normal ras p21 with similar limited success.

It should be apparent from the foregoing that while there are a number of diagnostic methods for determining the presence of ras oncogenes, or their transforming proteins, there is still a need for fast and reliable diagnostic methods that will permit the routine identification of a wide variety of ras related tumors.

SUMMARY OF THE INVENTION

In accordance with the instant invention, peptides are described that are useful as diagnostics for cancers which exhibit over expression of normal or oncogenic ras p21 protein.

A second aspect of the invention is a description of diagnostically and therapeutically useful peptides which inhibit the hydrolysis of GTP by ras p21 protein both in the presence and absence of GAP.

A third aspect of the invention is a description of diagnostically and therapeutically useful peptides which mediate the dissociation of GDP from ras p21-GDP complex.

A fourth aspect of the invention is a description of methods for assaying the ras p21protein using the peptides, that are useful in cancer diagnosis.

A fifth aspect of the invention is a description of the antibodies to the above peptides.

A sixth aspect of the invention is a description of methods for assaying the p21 protein using the antibodies, that are useful in cancer diagnosis.

A seventh aspect of the invention is a description of the method for using the peptides or fragments thereof, alone or in conjugation with ligands, in the treatment of human cancer.

Further aspects of the invention will become apparent upon consideration of the following description of the invention.

BRIEF DESCRIPTION OF THE DRAWINGS

FIG. 3 shows the GAP amino acid sequence used to generate DNA probes that were used to identify the lambda gt11 clone, GAP 6. Also shown is the corresponding DNA encoding sequence with possible codon redundancies.

FIG. 4 shows the DNA probes used to identify GAP 6.

FIGS. 5A–5D present the DNA and amino acid sequence of lambda clone, clone 101.

Figure 9A:
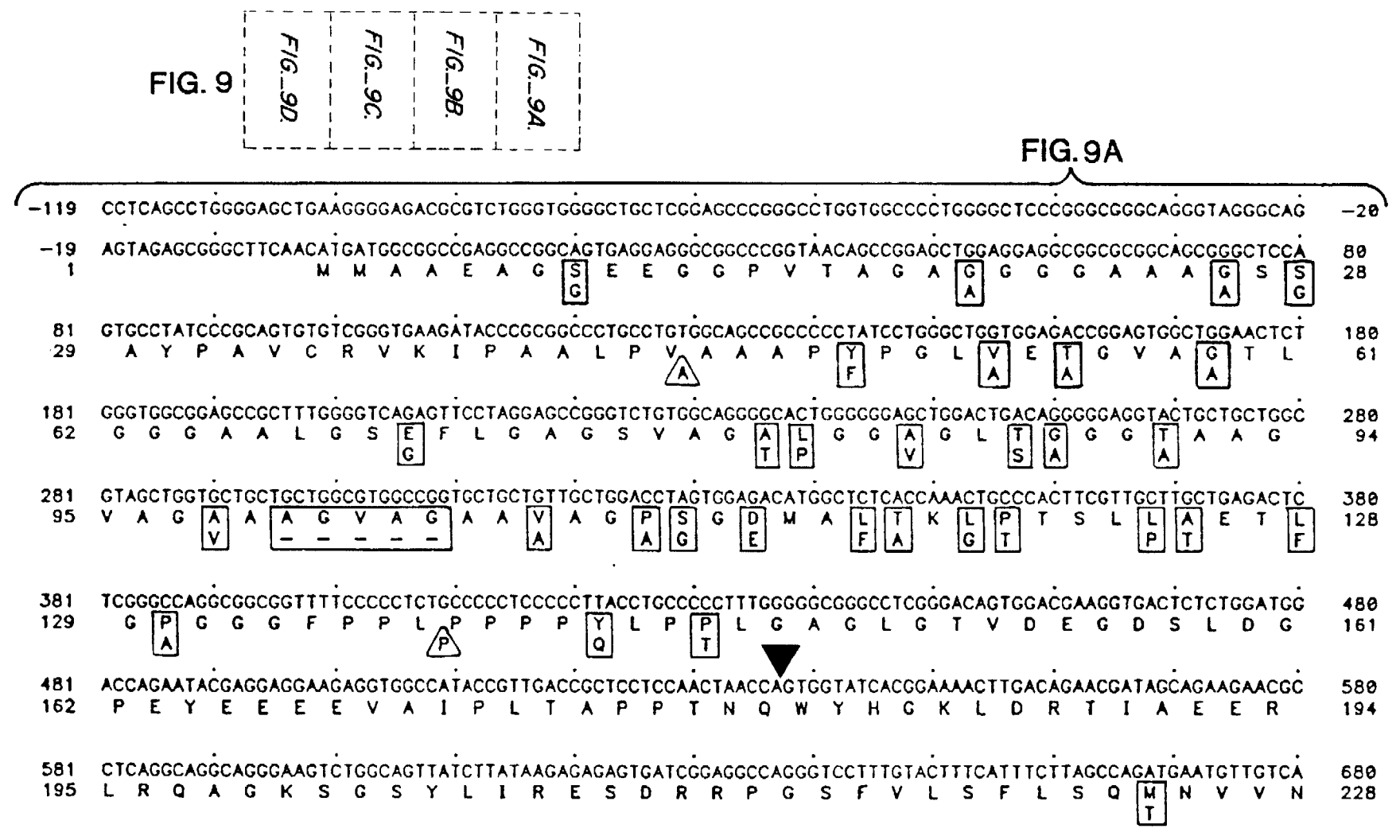
Figure 9C:
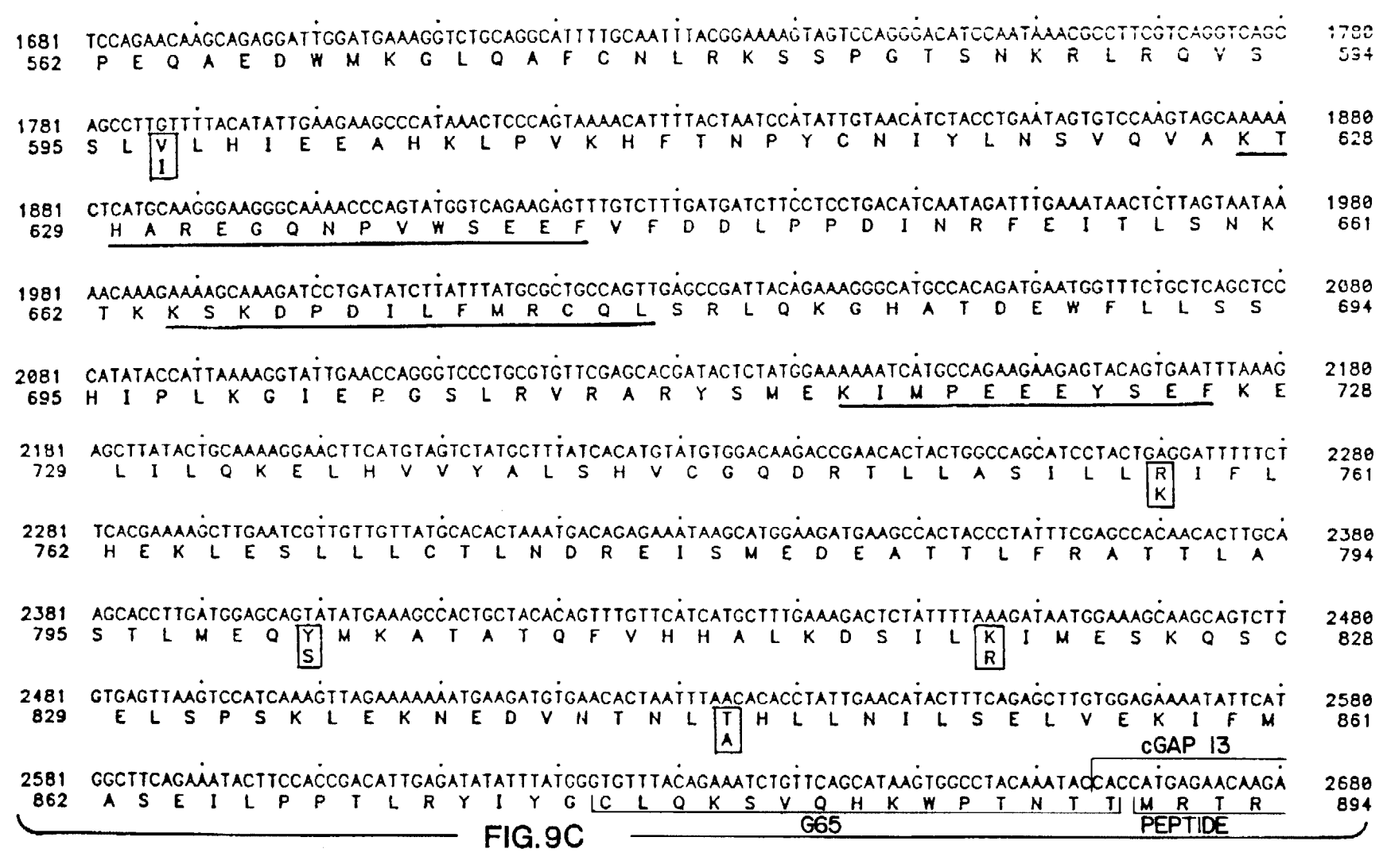
Figure 9D:
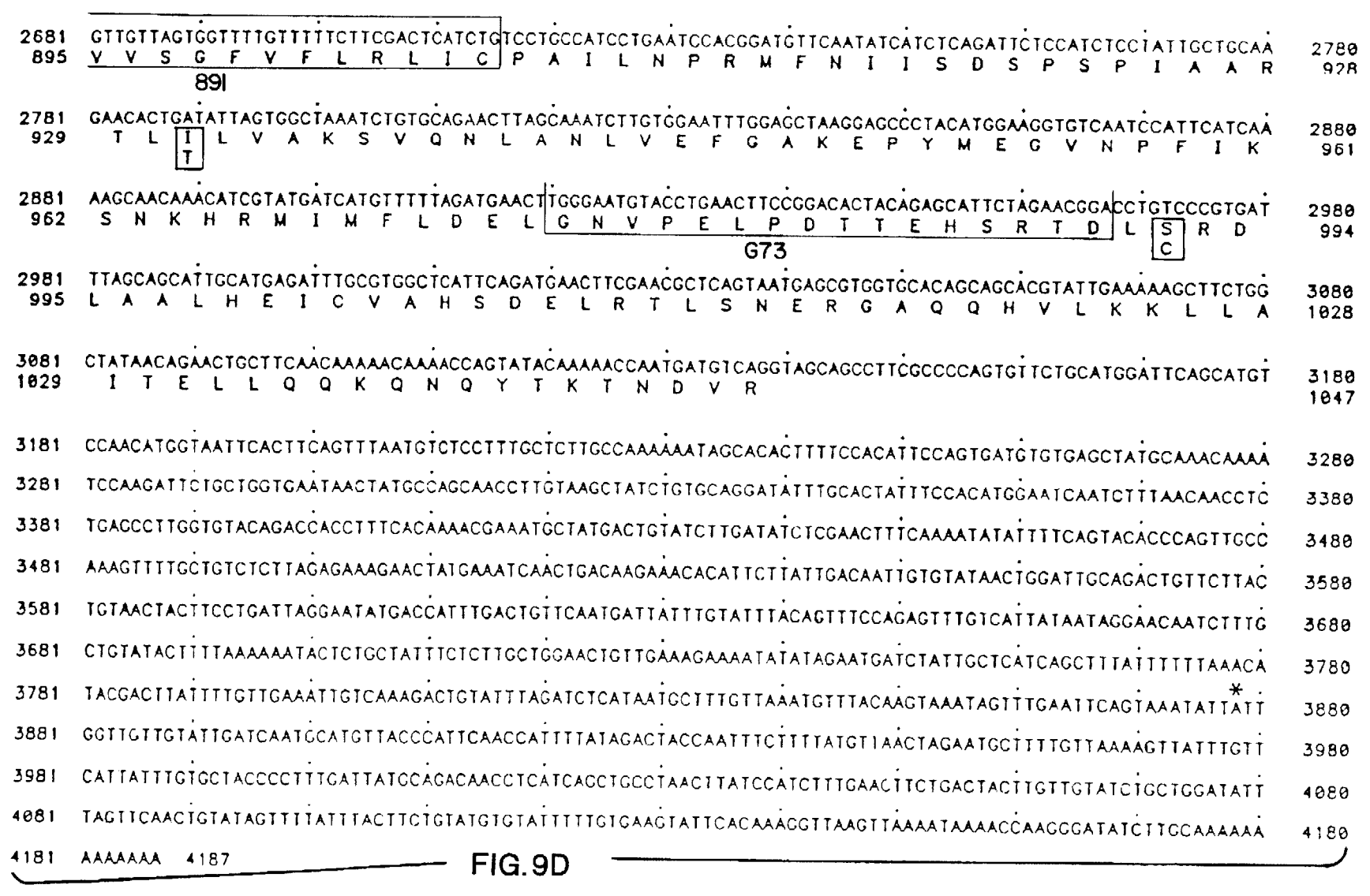

FIGS. 9A–9D present the DNA and amino acid sequence of lambda clone 101 and identifies the DNA and amino acid segments that correspond to the following peptides: sequences for G65, G73, cGAP 13, and peptide 891.

FIG. 10 identifies the positions of peptides G65, G73, cGAP13, and 891 using the amino acid numbering system common to FIGS. 5 and 9.

FIG. 11 shows the amino acid analysis of cGAP 13.

BRIEF DESCRIPTION OF THE INVENTION

Figure 1:
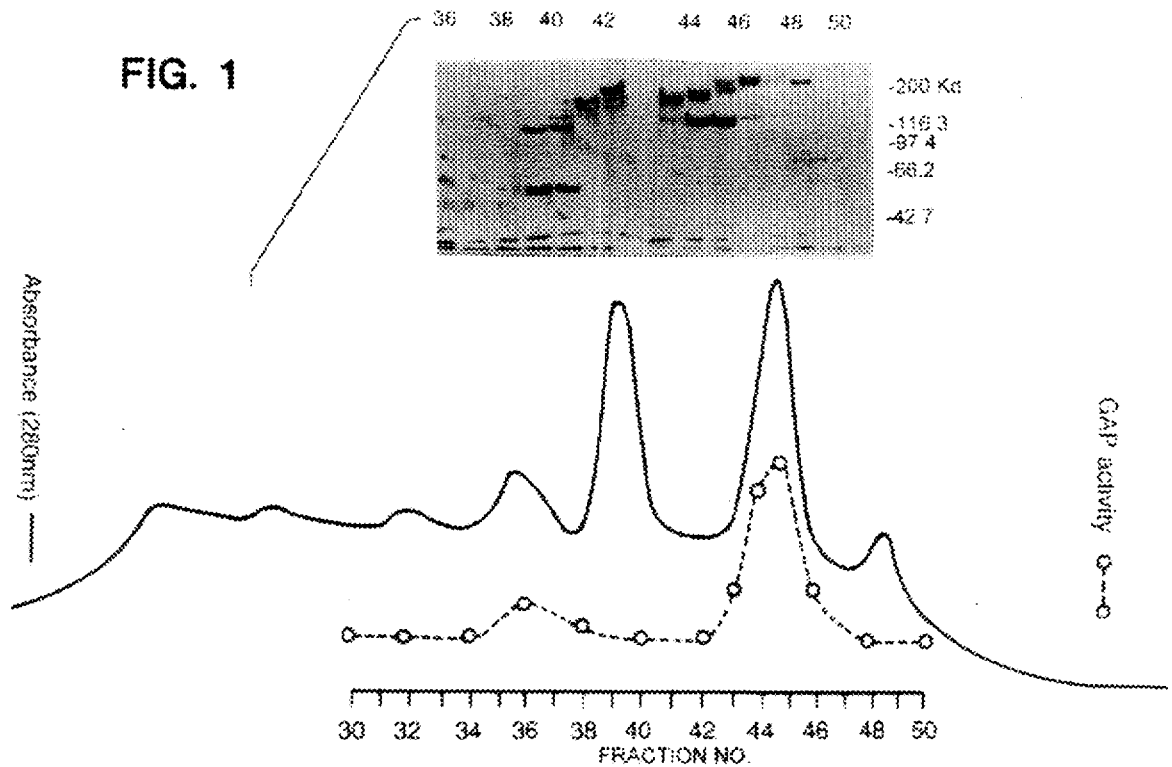
FIG. 1 shows the TSK phenyl column elution profile and silver staining of SDS PAGE fractions thereof.

The instant invention provides a description of peptides that bind to ras p21 protein, ras p21-GDP complex or ras p21-GTP complex. The invention further describes the antibodies to these peptides. The peptides and their antibodies, and the fragments derived therefrom, are useful as cancer diagnostics, being particularly useful to diagnose for cancers exhibiting an over expression of normal or oncogenic ras p21 protein. Further, the peptides and their fragments, alone or conjugated to ligands, are useful for cancer therapy. The identification and isolation of the instant peptides are facilitated by the availability of GAP sequences. Because such peptide sequences were generated based on a knowledge of the amino acid sequence of human GAP, or GAP like proteins, the order of discussion of the invention will be:

purification of GAP; methods of assaying GAP, the partial amino acid sequence of GAP; cloning of GAP using GAP probes based on the amino acid sequence and the identification of GAP DNA sequences in a cDNA library, along with subcloning of the sequences; the synthesis of peptide fragments of GAP; identification of the GAP peptide fragments which inhibit hydrolysis of GTP by ras p21, or ras p21-guanine nucleotide complexes; testing of such peptides for their abilities to mediate dissociation of GDP from ras p21-GTP complex, and GTPγS complex; the use of such peptides for assaying ras p21 protein; synthesis of antibodies to the peptides; the use of such antibodies for assaying p21 protein; and the use for the peptides or peptide fragments, alone or conjugated with ligands, for cancer therapy.

DETAILED DESCRIPTION OF THE INVENTION

A better understanding of the invention described herein will be realized by providing a brief description of some of the materials and methods used in the invention.

The normal cellular ras gene and its oncogenic counterparts are defined as described by N. Barbacid, 1987, *Ann. Rev. Biochem.*, 56:779. Similarly, the proteins encoded by these genes are also as described by Barbacid. Moreover, it will be appreciated that fragments of normal cellular p21 that bind GTP, and exhibit GAP stimulated GTPase activity are intended to come within the definition of ras p21 protein.

GAP is the acronym for guanine triphosphatase activating protein which is a protein having a molecular weight and amino acid sequence as described herein, and that has the further properties of stimulating GTPase activity of normal cellular ras p21 protein, while having little or no stimulatory activity when combined with oncogenic ras p21 proteins and GTP. Of course, it will be understood by those skilled in the art that GAP may also exist as aggregates or multimers under certain conditions, and these forms are intended to come within the scope of the definition. Moreover, the definition is further intended to cover fragments of GAP that exhibit activity. Exemplary of such a fragment is a molecule having a reduced subunit molecular weight of about 35,000 as shown herein.

The invention described herein includes peptides, synthetic or recombinantly produced, which are capable of binding to ras p21 protein, ras p21-GDP complex, or ras p21-GTP complex. These peptides take the following forms. The first is structurally similar to a fragment of GAP. The second form competes with the previous form in binding to ras p21 protein, ras p21-GDP complex, or ras p21-GTP complex. A third binds to the same site as would the first. This invention further includes antibodies, both polyclonal and monoclonal, specific to the above peptides, as well as methods for assaying ras p21 protein using the above peptides or the antibodies.

In relation to the peptide invention, it will be appreciated that the precise chemical structure of GAP, and the synthetic peptides may depend on a number of factors. As peptides contain ionizable amino and carboxyl groups, it is, of course, apparent that the peptides may be obtained in acid or basic salt form, or in neutral form. It is further apparent, that the primary amino acid sequence may be augmented by derivatization using sugar molecules (glycosylation) or by other chemical derivatizations involving covalent or ionic attachment to the peptides with, for example, lipids, phosphate, acetyl groups and the like, often occurring through association with saccharides. These modifications may occur in vitro or in vivo, the latter being performed by a host cell through post-translational processing systems. It will be understood that such modifications, regardless of how they occur, are intended to come within the definition of the peptides so long as the activities of the peptides, as defined herein, are not significantly altered.

As used herein, "ras p21-GTP complex" is defined as the GTP bound state of ras p21 protein.

As used herein, "ras p21-GDP complex" is defined as the GDP bound state of ras p21 protein.

As used herein, "ras p21-guanine nucleotide complex" is defined as guanine nucleotide bound state of ras p21 protein.

As used herein, "chromatography" is defined to include application of a solution containing a mixture of compounds to an adsorbent, or other support material which is eluted, usually with a gradient or other sequential eluant. Material eluted from the support matrix is designated eluate. The sequential elution is most routinely performed by isolating the support matrix in a column and passing the eluting solution(s), which changes affinity for the support matrix, either stepwise or preferably by a gradient, through the matrix. It will be appreciated that encompassed within the definition "chromatography" is the positioning of the support matrix in a filter and the sequential administering of eluant through the filter, or in a batch-mode.

The phrase "hydrophobic interaction matrix" is defined to mean an adsorbent that is a hydrophobic solid such as polystyrene resin beads, rubber, silica-coated silica gel, or crosslinked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high salt eluant containing anions such as chloride ion which bind to the anion exchange matrix and displace the adsorbed material.

By the phrase "high salt concentration conditions" is meant an aqueous solution wherein an ionic substance is present to create conditions of high ionic strength. Ionic strength is defined as is generally understood in the art and can be calculated from the putative concentrations of the various ions placed in solution modified by their activity coefficient. High salt concentrations that are routinely employed are typified by solutions containing high concentrations of ammonium sulfate; however, other salts, such as sodium chloride, potassium chloride, sodium sulfate, sodium nitrate, or sodium phosphate may also be employed.

The definition of "affinity chromatography" is understood to be similar to that of Wilchek et al., 1984, *Methods in Enzymology*, 104:3. In its broadest intended definition, "affinity chromatography" is a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids. "Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

The following relates to the antibody invention:

The word "antibody" as used herein refers to both polyclonal and monolconal antibodies. In addition, the term includes whole immunoglobin as well as antigen binding fragments thereof. The polyclonal antibodies may be produced by injecting a host animal such as rabbit, rat, goat, mouse, etc., with the peptide or peptide segment. The sera are extracted from the host animal and are screened to obtain polyclonal antibodies which are specific to the peptide immunogen. The monolconal antibodies may be produced by immunizing, for example, mice with the peptide mentioned above. The mice are inoculated intraperitoneally with an immunogenic amount of the peptide and then boosted with similar amounts of the immunogenic peptide. Spleens are collected from the immunized mice a few days after the final boost and a cell suspension is prepared therefrom for use in the fusion.

Hybridomas may be prepared from the splenocytes and a murine tumor partner using the general somatic cell hybridization technique of Kohler, B. and Milstein, C. 1975, *Nature*, 256:495–497. Available murine myeloma lines, such as those from the Salk Institute, Cell Distribution Center, San Diego, Calif., USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures (e.g., radioimmunoassay, enzyme immunoassay, or fluorescence immunoassay) using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

The binding of the antibodies to the protein may be enhanced if a sufficiently high concentration of affinity purified antibodies is used. Affinity purification is a technique well known in the art where the antigen peptide is bound to a carrier different from that used for immunization and the antibodies are run through the carrier so as to be purified

GAP Purification

Guanosine triphosphatase activating protein, or GAP, is widely expressed in higher eukaryotes. GAP has been detected in cell extracts from human and mouse normal tissues including brain, liver, placenta, B cells, and platelets. It has additionally been found in non-transformed cell cultures including NIH 3T3, as well as transformed cell lines, including human mammary cancer cells (MCF-7), retinoblastoma cells (Y79), and Wilm's tumor (G401). GAP is also present in insect cells such as, for example, *Spodoptera frugiperda*. From many of these cells or tissues, GAP may be isolated, albeit with minor variations in the purification protocols and the like.

The general scheme for GAP isolation and purification consists of releasing the molecule from the cytoplasm of appropriate cells, tissues or organs, followed by removing insoluble material and subjecting the soluble GAP fraction to cation exchange chromatography, followed by a second chromatographic step wherein the eluant from the cation exchanger is passed over an anion exchanger. GAP is eluted from the anion exchanger, and further purified by subjecting it to a third chromatographic step, either hydrophobic chromatography, or a second cation exchange step.

More specifically, GAP is prepared by releasing the molecule from the cytosol using any number of techniques including freeze thawing, sonication, mild detergent extraction, etc. This procedure is preferably carried out in a physiologically buffered solution containing one or more protease inhibitors. Moreover, to further inhibit protease activity, especially those proteases that rely on metal ions for activity, the extraction solution may contain metal ion chelators. The preferred extraction solution is a physiologically balanced salt solution containing the chelators ethyleneglycol tetraacetic acid (EGTA), or ethylenediamine tetraacetic acid (EDTA), plus the protease inhibitor phenylmethylsulfonylfluoride (PMSF). The metal ion chelator(s), as well as the protease inhibitor(s) are present at concentrations that effectively inhibit proteolysis, preferably about 5 mM and 100 μM, respectively. However, it will, of course, be appreciated by those skilled in the art that since the types and amounts of proteases vary depending on the starting material used to extract GAP, the concentrations that the protease inhibitors or chelators are used at, if indeed used at all, will also vary.

The mixture containing GAP is clarified by centrifugation, or in other ways to remove insoluble material from the aqueous cytosol fraction. If the cytosol fraction contains low amounts of GAP it can be concentrated by any one of several techniques well known to those skilled in the art, including high salt precipitation, such as, for example, with ammonium sulfate, or by ultra filtration. If GAP is concentrated by precipitation, it is preferably subsequently resuspended in a suitable physiologically balanced salt solution containing protease inhibitor(s) and preferably about 0.1% of a nonionic detergent, such as NP40. This solution is then prepared for ion exchange chromatography by dialyzing it against a compatibly buffered chromatographic solution, preferably containing millimolar phosphate, a metal ion chelator, a reducing agent, and a protease inhibitor. Additionally, because GAP activity is stimulated by the presence of divalent cations such as magnesium chloride, it may also be present in the solution. The pH of the solution is preferably about 6.0.

The GAP dialyzate is then subjected to chromatographic purification consisting preferably of three steps. The first involves purification using an ion exchange chromatographic step compatible with the GAP extraction buffer. Since the preferred extraction buffer contains phosphate, the initial step is purification of GAP by cation exchange chromatography. The second consists of ion exchange chromatography wherein the ion exchange matrix has the opposite ion binding capacity from that of the first ion exchanger employed.

Thus, the preferred purification scheme will consist of applying the phosphate solution containing GAP to a cation exchanger, and eluting GAP therefrom, preferably using solutions which alter the pH or conductivity of the solution. More preferably, GAP will be eluted by applying either a gradient or non-gradient salt solution, and most preferably will be eluted using a linear gradient of sodium chloride over the range of about 0–0.6 molar.

The preferred cation exchanger is a SP-cellulose cation exchanger. Such are commercially available from AMF Molecular Separations Division, Meridian, CT under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the GAP solution. The flow rate of the solution through the matrix will depend upon the size and geometry of the matrix used. It will be apparent to those skilled in the art, however, that care should be taken to avoid exceeding the unit capacity of the matrix with GAP. If the capacity is exceeded, GAP will not be totally retained and excess unretained GAP will be present in the effluent. The capacity of the matrix to retain GAP can be monitored by assaying for GAP in the effluent using one of the assays described below.

Fractions containing GAP are prepared for the second chromatographic step, that is, anion exchange chromatography. This consists of combining the fractions and adjusting the solution to a pH, and ionic strength compatible with anion exchange chromatography. A variety of anion exchangers are available, and depending on the type employed, the concentrations of these reagents will vary. DEAE-Sepharose or TSK-DEAE-5-PW may be employed. The general procedures for preparing and using these matrices are known to those skilled in the art. The preferred anion exchanger is TSK-DEAE-5-PW matrix. It is prepared by equilibrating it with a solution containing chloride ions at a pH of 8.5. More preferably, the solution will consist of Tris hydrochloride, pH 8.5plus a reducing agent, a metal chelator, magnesium chloride, and a protease inhibitor. The concentrations of the metal chelator and protease inhibitor will vary and depend on how extensively GAP is proteolyzed, and whether the proteases responsible are activated by metal ions. The concentration of monovalent cations, such as magnesium chloride and reducing agent can be determined empirically by monitoring GAP activity. Those concentrations which maintain the highest activity will be utilized Generally, it is preferred that magnesium chloride and the reducing agent be present in the range of about 0.5–1 mM, and 0.1–1 mM, respectively.

The solution is then passed through the anion exchange matrix whereupon GAP binds to the matrix. GAP is subsequently eluted from the matrix using solutions which alter the pH or conductivity. The preferred elution method consists of eluting GAP using a linear salt gradient ranging from 0–0.6 molar sodium chloride. The purity and activity of GAP so obtained can be monitored by the GTPase assay described below, and by sodium dodecyl sulfate polyacrylande gel electrophoresis run under reducing conditions. Using these techniques it was determined that GAP has a molecular weight of about 115,000–120,000 daltons.

The third chromatographic step consists of applying, after the anion exchange chromatography, either a second cation exchange step, or a hydrophobic interaction chromatographic step. The most preferred purification scheme utilizes a second cation exchange step. Application of either of these methods will generally increase the purity of GAP to about 95%. If a cation exchange column is chosen, the materials and methods described above are similarly applicable here. Generally, this will consist of decreasing the salt concentration present in the anion column eluates and adjusting the pH to about 6.0. Here, as in the initial cation chromatographic step, several different types of cation exchange matrices can be employed; however, the preferred matrix is a SP-TSK column which is run under high pressure. If hydrophobic chromatography is selected, the ionic strength of the eluate from the anion exchanger should be increased to be compatible with hydrophobic interaction chromatography. The solution can then be passed through a hydrophobic interaction chromatographic matrix, and eluted using techniques known in the art, including decreasing the salt concentration, or eluting with a chaotropic agent. Either of the latter solutions may be used alone, or in combination.

A variety of hydrophobic interaction chromatographic matrixes may be utilized. Generally, the materials and methods for utilizing hydrophobic chromatography are described by S. Shaltie, 1984, *Methods in Enzymology*, 104:69. While it is apparent there are many hydrophobic chromatographic materials and methods that may be employed to purify GAP, phenyl Sepharose is preferred, and it is further preferred that the chromatography be employed under high pressure. The general procedures for forming high pressure liquid chromatography involving a phenyl derivatized matrix are described by F. Regmaer, 1983, *Methods in Enzymology*, 91:137. The preferred phenyl derivatized matrix is available commercially from Bio-Rad Corporation, and is sold under the trade name Biogel TSK phenyl-5-PW.

It will be additionally appreciated by those skilled in the art that an alternative purification scheme may consist of a cation and anion chromatographic exchange step, followed by an affinity chromatographic step. This may be achieved by binding GAP to one or more plant lectins having a known carbohydrate specificity compatible with carbohydrates which may be present on GAP, or by binding GAP to anti-GAP antibodies. In either event, GAP can then be released from the affinity matrix using the appropriate sugar if the matrix is composed of a lectin, or by pH or chaotropic agents if the matrix is composed of antibody.

Because GAP is a protease-sensitive molecule that is broken down into lower molecular weight species having GAP activity, in a preferred embodiment of the invention the entire purification procedure is carried out rapidly in the cold to reduce protease activity. In general, this temperature is in a range below 10° C., with a preferred temperature range being about 2°–8° C. Most preferred is a temperature of about 4° C.

Finally, it should be noted that while the preferred applications of the ion exchange materials described herein are in a column format, it will be appreciated that they may also be used in batch format as well.

A preferred embodiment purification scheme consists of isolating GAP from human placentas as follows.

GAP was isolated from 300 g of human placentas by the following three-step chromatographic procedure. Placentas were obtained shortly after delivery, and kept on ice until they were processed. After it was determined by standard tests that the placentas were free of HIV antibodies, they were processed as follows. The initial step consisted of mechanically removing connective tissue, and ridding the placentas of excess blood by multiple soakings in phosphate buffered saline (PBS). The placentas were then fragmented by freezing the tissue at −70° C., followed by placing the tissue in solution of PBS containing 5 mM EGTA, 100 µM PMSF and disrupting the tissue in a blender until a uniform, fine suspension was apparent. The suspension was centrifuged at 100,000×g to remove insoluble debris, the supernatant removed and the proteinaceous material therein precipitated with 40% ammonium sulfate. The ammonium sulfate was removed, and the precipitated proteins resuspended in PBS containing 0.1% NP40 and 100 µM PMSF. This solution was immediately dialyzed against 20 mM potassium phosphate, 1 mM $MgCl_2$, 5 mM EGTA, 0.1 mM DTT, 100 µM PMSF, pH 6.1 for six hours. This solution was then immediately chromatographed on a cation matrix, S-Sepharose (fast flow, obtainable from Pharmacia Corporation), pre-equilibrated in 20 mM potassium phosphate, 1 mM $MgCl_2$, 5 mM EGTA, 0.1 mM DTT, 100 µM PMSF, pH 6.1.

Proteins absorbed to the cation exchanger were eluted with a linear salt gradient containing 0–0.6M sodium chloride. Using the GAP assay described below, most of the GAP activity was shown to be present in two peaks, a major peak eluting at a sodium chloride concentration of 100–150 mM, and a minor peak eluting at a sodium chloride concentration of 220–300 mM. The major peak was dialyzed against 30 mM Tris-HCl, 1 mM magnesium chloride, 1 mM EGTA, 0.1 mM DTT, 100 µM PMSF, pH 8.5. The dialyzate was applied to an anion exchange column, TSK-DEAE-5-PW (150×21.5 mm). The anion exchange matrix was treated with a linear salt gradient ranging from 0–0.6M sodium chloride to elute the adherent proteins. Most of the GAP activity eluted at a sodium chloride concentration of about 130 mM NaCl. Those fractions containing GAP activity were pooled, brought to 0.5M ammonium sulfate, and passed through a hydrophobic column, phenyl-TSK HPLC. Proteins were eluted from the hydrophobic column using a crisscross gradient consisting of increasing ethylene glycol 0–30%, and decreasing ammonium sulfate, 0.5M–0. The majority of GAP activity eluted at a concentration of 24% ethylene glycol and 0.1 molar ammonium sulfate. GAP activity assays, as performed below, correlated with a protein band of about 120,000 daltons, as revealed by sodium dodecyl sulfate polyacrylamide gel electrophoresis on 6% gels run under reducing conditions (FIG. 1).

A second embodiment purification scheme was employed to purify GAP. Human placentas were again obtained shortly after delivery, and soaked in ice cold PBS, and homogenized and clarified as described in Example I. Ammonium sulfate was again added to the clarified homogenate to a final concentration of 40% to precipitate proteinaceous material.

The ammonium sulfate solution was allowed to stand for one hour at 4° C. prior to recovering the precipitated proteinaceous material by centrifugation for 15 minutes at 10,000×g. The pellet was resuspended in PBS containing 0.1% NP40 and 100 µM PMSF. This solution was dialyzed for six hours at 4° C. against 20 mM potassium phosphate, pH 6. 1, containing 1 mM $MgCl_2$, 5 mM EGTA, 0.1 mM DTT, and 100 µM PMSF. Because GAP is susceptible to proteolysis, longer dialysis times are not desirable.

The GAP dialyzate was diluted three-fold with 4 mM potassium phosphate, pH 6.1, containing 0.02M $MgCl_2$, 1 mM EGTA, 0.1 mM DTT, and 100 µM PMSF to lower the conductivity of the solution to 1 millisiemens. This conductivity is compatible with application of the dialysate to a S-Sepharose cation exchange column. The dialysate was clarified by centrifugation at 10,000×g for 10 minutes, followed by a further clarification step consisting of filtration through a 0.45 µm filter, prior to adding the dialysate to the S-Sepharose column (fast-flow, Pharmacia). Most of the contaminating proteins passed through the S-Sepharose column, and the adsorbed proteins eluted with a 1.5 liter salt gradient consisting of 0–0.6M NaCl. Those fractions containing GAP activity were identified using the GAP assay described below.

As observed in the first example, GAP eluted from the cation exchange column in predominantly two major peaks. The first peak eluting over a sodium chloride concentration of 100–150 mM was pooled and dialyzed against 30 mM Tris-HCl buffer, pH 8.5, containing 1 mM EGTA, 1 mM $MgCl_2$, 0.1 mM DTT and 100 µM PMSF. The solution was dialyzed at 4° C., and clarified by filtration with a 0.45 µm filter. The filtrate was divided into equal halves, and each half purified using two consecutive anion exchange columns.

Figure 2:
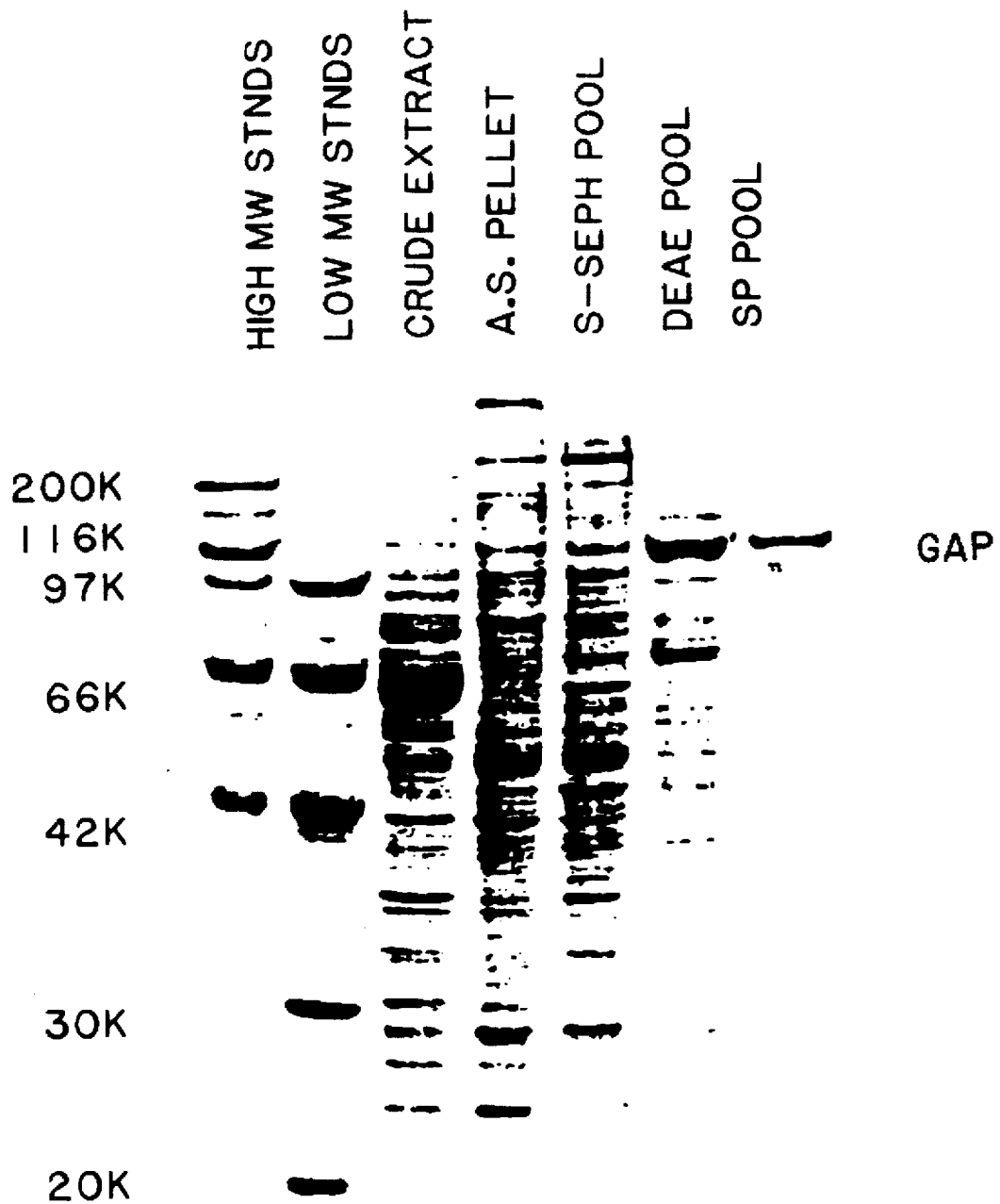
FIG. 2 shows the SDS gel profile of GAP purified by a three-step chromatographic scheme consisting of cation, and anion chromatography, followed by a second cation chromatographic step.

The two filtrates were separately loaded onto a TSK-DEAE-5-PW column having the dimensions 150×21.5 mm. The column was pre-equilibrated in the Tris-hydrochloride, pH 8.5 dialysis buffer described above. GAP was eluted from the column with a 60-minute 0–0.6M NaCl gradient with a flow rate of 3 ml/minute. The majority of the GAP activity from both filtrates eluted as a single peak at a sodium chloride concentration of about 130 mM. Sodium dodecyl sulfate, polyacrylamide gel electrophoretic analysis of the DEAE fractions showed that GAP was the major protein in the peak activity fractions. Fractions containing GAP from both purifications were pooled and diluted 5-fold into 2 mM potassium phosphate, pH 6.1, containing 0.1 mM EGTA, 10 µM DTT, 10 µM PMSF to lower the salt concentration to insure that the solution was chromatographically compatible with a second cation exchange chromatographic step, that is, chromatography with a SP-TSK column. The pH of the solution was checked and adjusted to pH 6.1 with sodium acetate (3M, pH 4.8) if necessary. Both of the GAP fractions isolated from the DEAE columns were further purified separately over a cation column, TSK-SP-5-PW having dimensions of 75×7.5 mm. A solution containing 20 mM potassium phosphate, pH 6.1, containing 1 mM EGTA, 0.1 DTT, and 0.1 mM PMSF was passed through the column, followed by eluting GAP with a 45-minute, 0–0.6 M sodium chloride gradient at 1 ml per minute. Those fractions containing GAP were identified using the assay described below and sodium dodecyl sulfate polyacrylamide gel electrophoresis. GAP activity corresponded to a protein having a molecular weight of about 116,000 daltons. Amino acid analysis was performed on purified GAP to determine protein concentration. Starting with about 300 grams of human placenta, approximately 430 micrograms of purified GAP was obtained. FIG. 2 shows the SDS PAGE analysis of GAP at the various stages of purification described above.

GAP Assay

Several assays have recently been described to measure GAP activity. M. Trahey and F. McCormick, 1987 *Science*, 238:542; Adari et al., 1988 *Science*, 240:518. These references are herein incorporated in their entirety. GAP may be assayed in vitro, and several different types of in vitro assays can be performed. The preferred assay involves measuring the presence of GDP resulting from the hydrolysis of GTP. This assay involves combining in an appropriate physiologically buffered aqueous solution, empirically determined optimal amounts of normal cellular p21, and α-32P-GTP, plus GAP. The solution may also contain protease inhibitors and a reducing agent. Also, since cations greatly stimulate GAP activity they should be present in an effective amount. The preferred cation is magnesium chloride. The reaction solution is incubated for various times and may be conducted at temperatures typically employed to perform enzymatic assays, preferably 10°–40° C., and more preferably at 37° C. At the appropriate times aliquots are removed and assayed for α-32P-GDP. This is readily accomplished by first separating p21 containing bound α-32P-GDP from the other reactants in the solution, particularly free α-32P-GTP. This can be achieved by immunoprecipitating p21 with antibodies directed thereto. Immune precipitation techniques and anti-p21 antibodies are known, and routinely employed by those skilled in the art. α-32P-GDP, is released from the immune precipitate preferably by dissolving the sample in a denaturing detergent at an elevated temperature, more preferably in 1% sodium dodecyl sulfate at 65° C. for five minutes, and chromatographing the mixture on a suitable thin layer chromatographic plate. The chromatography is preferably carried out on a PEI cellulose plate in 1M LiCl. α-32P-GDP is identified by its mobility relative to a known standard using suitable radiodetection techniques, preferably autoradiography.

An alternative assay for GAP activity is to substitute gamma labeled 32P-GTP for α-labeled 32P-GTP in the above assay system, and assay for free 32P labeled phosphate using activated charcoal. This assay can be carried out as described by Tjian et al., 1980, *Cold Spring Harbor Symp. Quant. Biol.*, 44:103.

An additional assay does not involve immune precipitation. Rather, an aliquot from a GAP assay reaction mixture described above can be directly subjected to PEI cellulose chromatography in 1 M LiCl. This assay, however, is most useful for assaying solutions having substantially purified GAP.

A typical GAP assay can be carried out as follows. Approximately 0.8 micrograms of H-ras protein obtained as described by Trahey, et al., *supra* was bound to α-32P-GTP followed by precipitation of the complex with 13 micrograms of an anti-ras antibody, 157-181, that recognizes the carboxyl terminal end of the molecule. Specifically, 157-181 recognizes the carboxyl terminal residues at positions 157–181. Adari et al., 1988 *Science*, 280:518. Next, 10 micrograms of sheep-anti-mouse IgG, and 10 microliters of protein A-Sepharose beads were added. As a control, the same reactants were combined except that rat IgG replaced 157-181, and goat anti-rat IgG replaced sheep anti-mouse IgG. The pellets were washed with 20 mM tris hydrochloride, pH 7.4, containing 20 mM sodium chloride, 1 mM magnesium chloride and 1 mM DTT and resuspended in the same solution. Four microliter aliquots of the immune complex were then mixed with 10 microliters of GAP, or, as a control, buffer without GAP. After 60 minutes incubation at room temperature the Sepharose beads were washed again, and the bound nucleotides analyzed using thin layer chromatography with 1M LiCl as the solvent. The thin layer plate was autoradiographed for one to two hours after which it was developed. The autoradiograph revealed that addition of sufficient GAP causes the near complete hydrolysis of GTP to GDP, whereas very little GTP hydrolysis occurs in the control lacking GAP. The assay detects GAP in a semi-quantitative, dose-dependent fashion. Quantitation can be improved by scraping the relevant regions of the plate and measuring cpm in GDP by use of a gamma counter. The immune precipitation controls having rat IgG substituted for the mouse antibodies revealed no GTP or GDP.

In addition to the above method, GAP can be preferably assayed as follows. Four μM normal cellular p21 was dissolved in a buffer containing 80 mM β-glycerophosphate, 5 mM MgCl$_2$, 1 mM DTT, pH 7.5, plus 255 μM [α-32P] GTP (16 Ci/mmole), 4 mM ATP, and bovine serum albumin (2.5 mg/ml). The mixture was preincubated for 30 minutes at 37° C., followed by the addition of either a sample suspected of containing GAP, or an equal volume of buffer. After one hour at room temperature the monoclonal antibody Y13-259 in the presence of 0.5% NP40 was added in an amount sufficient to bind all the p21 present in the solution. Next, goat anti-Rat IgG-Protein A Sepharose was added to collect p21 bound to Y13-259, and the immune complex isolated and washed ten times in 20 mM Tris-HCl, pH 8.0, 100 mM NaCl, 5 mM MgCl$_2$, and 0.5% NP40. To determine the extent of GTP binding and hydrolysis during these steps a control was run consisting of adding 5 μg of p21 immediately before adding Y13-259.

Nucleotides were eluted from p21 with 1% SDS, 20 mM EDTA at 65° C. for five minutes and chromatographed on PEI Cellulose in 1M LiCl. GTP and GDP were visualized using standard autoradiographic techniques. The results showed that normal cellular p21 effects a nearly complete conversion of GTP to GDP when compared to mutant ras oncogenic proteins Asp 12 and Val 12 assayed similarly. Moreover, little or no GTP or GDP was detected in the control sample.

The assays described above are presented in more detail by Trahey and McCormick, 1987 in *Science*, 238:542, and by Adari et al., 1988 in *Science*, 240:518. Both of these references are hereby incorporated by reference.

GAP Amino Acid Sequence

The GAP protein, or fragments derived therefrom can be sequenced using standard techniques known to those skilled in the art In the event that GAP is isolated having a blocked amino terminal end, internal sequencing can be achieved by fragmenting the molecule such as, for example, with lysyl endopeptidase, and sequencing one or more of the resulting fragments. Although this may not necessarily be the case for GAP isolated from sources other than placenta, in the instant invention it was determined that GAP exhibited a blocked amino terminal end.

The protein having a molecular weight of about 120,000 obtained by the purification method described above was electro-eluted from a 6% sodium dodecyl sulfate, polyacrylamide gel in 0.05 molar ammonium bicarbonate containing 0.1% sodium dodecyl sulfate. The procedure followed is described by Hunkapillar et al., 1983 *Methods in Enzymology*, 91:227. The electro-eluted protein was fragmented for internal sequencing using lysyl endopeptidase (5% w/w, 18 hours at 40° C., WAKO). Peptides were fractionated by reverse-phase high performance liquid chromatography using a Brownlee Aquapore RP-300 cartridge (100×2.1 mm, Applied Biosystems). Peptides were eluted with an Acetonitrile gradient from 0–70% in 120 minutes (Buffer A, 0.1% trifluoroacetic acid (TFA) in H$_2$O; Buffer B, 0.085% TFA in 85% acetonitrile). Automated sequence analysis of the peptides was conducted on an Applied Biosystems 470A gas-phase sequencer as reported. A peptide characteristic of GAP has the following amino acid sequence: IMPEEEYSEFK.

Cloning of GAP

A full length cDNA sequence that encodes GAP was obtained as follows: first, partial cDNA sequences were identified in a cDNA library using as oligonucleotide probes, DNA sequences derived from the partial amino acid composition of GAP. One such partial cDNA sequence, referred to as GAP 6, was subcloned and sequenced. Knowledge of its DNA sequence led, in turn, to additional probes that were used to screen cDNA libraries for longer cDNA inserts, eventually yielding the full length clone, clone 101. Each of the various procedures will be discussed below.

1. General Cloning Techniques

Construction of suitable vectors containing the desired GAP coding sequence employs standard ligation and restriction techniques which are well understood in the art. Isolated vectors, DNA sequences, or synthesized oligonucleotides are cleaved, tailored, and religated-therefor in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs. Product Catalog. In general, about 1 µg of plasmid or DNA sequence is cleaved by one unit of enzyme in about 20 µl of buffer solution. In the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15 to 25 minutes at 20 to 25° C. in 50 mM Tris pH 7.6,50 mM NaCl, 6 mM MgCl$_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 µl volumes under the following standard conditions and temperatures: 20 mM Tris-Cl pH 7.5, 10 mM MgCl$_2$, 10 mM DTT, 33 µg/ml BSA, 10 mM–50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 µg/ml total DNA concentration. In blunt end ligations, the total DNA concentration of the ends is about 1 µM.

In vector construction employing "vector fragments," the vector fragment is commonly treated with bacterial alkaline phosphatase (BAP) in order to remove the 5' phosphate and prevent religation-therefor of the vector. BAP digestions are conducted at pH 8 in approximately 150 mM Tris, in the presence of Na$^+$ and Mg$^{+2}$ using about 1 unit of BAP per µg of vector at 60° C. for about 1 hour. Nucleic acid fragments are recovered by extracting the preparation with phenol/ chloroform, followed by ethanol precipitation. Alternatively, relegation can be prevented in vectors which have been double digested by additional restriction enzyme digestion of the unwanted fragments.

In the constructions set forth below, correct ligations are confirmed by first transforming the appropriate *E coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., (1981 *Nucleic Acids Res.* 9:2989) and analyzed by restriction and/or sequenced by the dideoxy method of F. Sanger et al., 1977, *Proc. Natl. Acad. Sci.* (*USA*), 74:5463 as further described by Messing et al., 1981, *Nucleic Acids Res.*, 9:309, or by the method of Maxam et al., 1980, *Methods in Enzymology*, 65:499.

Host strains used in cloning in M13 consists of *E. coli* strains susceptible to phage infection, such as *E. coli* K12 strain DG98 are employs The DG98 strain has been deposited with ATCC Jul. 13, 1984 and has accession number 1965.

Depending on the host cell used, transformation is done using standard techniques appropriate to such cells. The calcium treatment employing chloride, as described by S. N. Cohen, 1972, *Proc. Natl. Acad. Sci.* (*USA*) 69:2110, or the RbCl$_2$ method described in Maniatis et al., 1982, *Molecular Cloning: A Laboratory Manual* Cold Spring Harbor Press, p. 254 was used for procaryotes. Transfection of Sf9 cells was achieved using a modification of the calcium phosphate precipitation technique (Graham, F. L. et al., 1973 *Virology* 52:456) as adapted for insect cells (J. P. Burand et al., 1980, *Virology* 101; E. B. Casstens et al., 1980, *Virology* 101:311). Additional details regarding transfection of Sf9 cells are described by Summers and Smith in "A Manual of Methods for Baculovirus Vectors and Insect Cell Culture Procedures", Texas A & M Press: 1986. The baculovirus transfer vectors employed herein are derived from transfer vectors which have been described by G. E. Smith et al., 1983, above. These vectors were originally constructed by cloning the AcNPV EcoRI-1 fragment containing the polyhedron gene into the EcoRI site of *E. coli* plasmid pUC8 as described by Vieira et al., 1982, *Gene* 19:259–268. A family of plasmids having single BamHI cloning sites at various locations in the polyhedron gene were created as described by Smith et al., 1983, above. The most used of these, pAc373, has a unique BamHI site 50 base pairs downstream from the polyhedron cap site, that is to say, 8 base pairs before the polyhedron ATG translation initiation codon (Luckow and Summers in *Biotechnology*, Vol. 6, p. 47 (1988).

2. Oligonucleotide Probes

Synthetic oligonucleotides were prepared by the triester method of Matteucci et al., 1981, *J. Am Chem. Soc.* 103:3185 or using commercially available automated oligonucleotide synthesizers. Kinasing of single strands prior to annealing or for labeling is achieved using an excess, e.g., approximately 10 units of polynucleotide kinase to 0.1 mmole substrate in the presence of 50 mM Tris, pH 7.6, 10 mM MgCl$_2$, 5 mM dithiothreitol, 1–2 mM ATP, 1.7 pmoles gamma $^{32}$P-ATP (2.9 mCi/mmole), 0.1 mM spermidine, 0.1 mM EDTA.

Using the partial GAP amino acid sequence described above, and known codon redundancies thereto, several DNA oligonucleotide probes were synthesized and these are shown in FIGS. 3 and 4.

3. Identification and Isolation of GAP Sequences

Several procedures are available for identifying GAP DNA sequences. The preferred procedure is to use the oligonucleotide probes described above to screen cDNA libraries. cDNA libraries can be constructed using techniques known in the art, or can be purchased commercially.

An illustrative procedure for making a cDNA library containing GAP sequences may consist of isolating total cytoplasmic RNA from suitable starting material, and further isolating messenger RNA therefrom. The latter can be further fractionated into Poly (A+) messenger RNA, which in turn is fractionated further still into Poly (A+) messenger RNA fractions containing GAP messenger RNA. The appropriate GAP messenger RNA can then be reverse transcribed and clued into a suitable vector to form the cDNA library.

More specifically, the starting material (i.e., tissue, cells) is washed with phosphate buffered saline, and a non-ionic detergent, such as ethylene oxide, polymer type (NP-40) is added in an amount to lyse the cellular, but not nuclear membranes, generally about 0.3%. Nuclei can then be removed by centrifugation at 1,000×g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA. Polyadenylated (Poly A+) messenger RNA (mRNA) can be obtained from the total cytoplasmic RNA by chromatography on oligo (dT) cellulose (J. Aviv et al., 1972, *Proc. Natl. Acad. Sci.* 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and slowly passed through an oligo (dT) cellulose column previously equilibrated with binding buffer (500 mM NaCl, 10 mM Tris, 1 mM EDTA, pH 7.5) The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2M and 2 volumes of 100% ethanol. The RNA is reprecipitated twice, washed once in 70% and then 100% ethanol prior to drying. The poly (A+) MRNA can then be used to construct a cDNA library.

cDNA can be made from the enriched mRNA fraction using oligo (dT) priming of the poly A tails and AMV reverse transcriptase employing the method of H. Okayama et al., 1983, *Mol. Cell Biol.* 3:280, incorporated herein by reference.

Other methods of preparing cDNA libraries are, of course, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Ser. No. 564,224, now U.S. Pat. No. 4,518,584, filed Dec. 20, 1983, and assigned to the same assignee, incorporated herein by reference.

As mentioned above, cDNA libraries are commercially available. A particularly useful library is sold by Clontech (Catalog number #L H1008). It is a lambda gt11 human placenta cDNA library made from total poly (A+) messenger RNA.

4. Identification of GAP DNA Sequences

The oligonucleotide probes described above, GW13, GW15, GW17 and GW19 were used to screen the commercially available Clontech library. The library was plated at about 50,000 plaques per plate using 17 plates. Thus, about 850,000 plaques were screened using the plaque hybridization procedure. While a variety of such procedures are known, a description of the preferred procedure follows. Each 150 mM plate was replicated onto duplicate nitrocellulose filter papers (S & S type BA-85). DNA was fixed to the filter by sequential treatment for 5 minutes with 0.5N NaOH plus 1.0M NaCl; 1.5M NaCl plus 0.5M Tris-HCl pH 8; and 20 mM Tris plus 2mM EDTA pH 8. Filters were air dried and baked at 80° C. for 2 hours.

The duplicate filters were prehybridized at 55° C. for 2 hours with 10 ml per filter of DNA hybridization buffer, 5×SSC, pH 7.0, 5×Denhardt's solution (polyvinylpyrrolidone, plus Ficoll and bovine serum albumin; 1×0.02% of each), 50 mM sodium phosphate buffer at pH 7.0, 5 mM EDTA, 0.1% SDS, and 100 μg/ml yeast RNA. The prehybridization buffer was removed and the samples were hybridized with a mixture of kinased probes under conditions which depend on the stringency desired. About $2 \times 10^6$ cpm/ml total was used. Typical moderately stringent conditions employ a temperature of 42° C. plus 50% formamide for 24–36 hours with 1–5 ml/filter of DNA hybridization buffer containing probe. For higher stringencies high temperatures and shorter times were employed. The preferred hybridization conditions consisted of hybridizing the probes to the filters in 5×SSC (standard saline citrate), Denhardt's solution, 50 mM NaPO$_4$ pH 7.0, 5 mM EDTA, 0.1% SDS, and 100 mg/ml yeast RNA at 55° C. overnight. Next, the filters were washed twice, 30 minutes each wash, at room temperature with 2×SSC, 0.1% SDS and 50 mM sodium phosphate buffer pH 7, then washed once with 2×SSC and 0.1% SDS at 50° C., and air dried. Finally, the filters were autoradiographed at −70° C. for 36 hours.

The autoradiographic results revealed a single positive plaque. Using the washing and hybridization conditions described above, several lambda gt11 plaque purified isolates were identified and picked. Viral DNA was obtained from one of these, termed GAP 6, as follows. GAP 6 was plated at high density on a lawn of *E. coli* strain Y 1090 (r) Following lysis of the *E coli*, phage particles were eluted into S M buffer (0.1M NaCl 8.1 mM MgSO$_4$ 50 mM Tris-HCl pH 7.5 0.01% Gelatin) by covering the *E. coli* with buffer and incubating the plate in the cold for several hours. The lysate containing phage particles was centrifuged at 11,500×g for 20 minutes to remove cellular debris, and the resulting supernatant titered using standard techniques. A titer of $2 \times 10^{10}$ PFU, was determined. Finally, phage DNA was isolated by the procedure of Maniatis et al., above.

5. Characterization of GAP 6

GAP 6 was subcloned into a suitable vector in order to characterize the DNA both as to EcoRI restriction sites, and partial DNA sequence. Although GAP 6 DNA can be cloned into a variety of vectors, in the instant invention it was cloned into M13. More specifically GAP DNA was cloned into a M13 vector as follows. GAP 6 DNA was treated with EcoRI enzyme which produced two fragments, about 2.0 kb and 0.24 kb. These fragments were isolated using standard agarose gel techniques, and ligated into M13mp18. The M13 vector was designed so that vectors without DNA inserts show up blue under the proper culture conditions, whereas vectors with a DNA insert are clear.

The ligated M13mp18 phage were transduced into frozen competent *E. coli* K12 strain DG98 and cultured by plating on media containing $5 \times 10^{-4}$M isopropyl thiogalactoside (IPTG) obtained from Sigma Chem. (St. Louis, Mo.) and 40 μg/ml X gal. Non alpha-complementing white plaques were picked onto fresh media. Mini-cultures were screened for recombinant single strand phage DNA containing inserts.

The white M13 plaques were screened for inserts by direct gel electrophoresis. The latter procedure was conducted essentially as described by J. Messing, 1983, *Methods of Enzymology* 101:20, which is hereby incorporated by reference. Four M13mp18 subclones were identified by this method. Two subclones, GAP 2 and GAP 8, contained the 2 kb fragment in both orientations. The remaining two subclones, GAP 12 and GAP 18, contained the 0.24 kb fragment in both orientations.

The partial DNA sequence of GAP 2 and GAP 8 was determined by the T. Sanger, S. Nicklen, and H. R. Coulson, 1977, *Proc. Natl. Acad. Sci. USA* 74:5463–5467 techniques described above:

```
5' AAAACTCATGC AAGGGAAGGG CAAAACCCAG TATGGTCAGA
   AGAGTTTGTC TTTGATGATC TTCCTCCTGA CATCAATAGA TTTGAAATAA
   CTCTTAGTAA TAAAACAAAG AAAAGCAAAG ATCCTGATAT CTTATTTATG
   CGCTGCCAGT TGAGCCGATT ACAGAAAGGG CATGCCACAG ATGAATGGTT
   TCTGCTCAGC TCCCATATAC CATTAAAAGG TATTGAACCA GGGTCCCTGC
   GTGTTCGAGC ACGATACTCT ATGGAAAAAA TCATGCCAGA AGAAGAGTAC
   AGTGAATTTA AAGAGCTTAT ACTGCAAAAG GAACTTCATG TAGTCTATGC
   TTTATCACAT 3'
```

6. Identification of GAP DNA Sequences Longer Than GAP 6

General Technique: A novel procedure was used to identify plaques that contain GAP cDNA inserts larger than those present in GAP 6 which consisted of elucidating inserts present in either the lambda gt11 library described above, or a lambda gt10 library described below. The procedure consisted of synthesizing cDNA inserts using DNA oligonucleotides having sequences complementary to the 5' region of GAP 6, and oligonucleotide primers that flank the EcoRI insertion sites of lambda gt11, or lambda gt10, using the polymerase chain reaction, or PCR. The newly identified PCR products were sequenced, and accordingly DNA probes were synthesized having sequences 5' of GAP 6. These probes were, in turn, used to identify plaques containing larger GAP cDNA inserts. The procedure was repeated several times using as probes, DNA sequences progressively further 5' of GAP 6 identified from each round of newly synthesized cDNA inserts.

PCR is described in U.S. Pat. Nos. 4,683,202 and 4,683,195, both of which are hereby incorporated in their entirety. In general, the synthesis/amplification of DNA sequences by PCR involves an enzymatic chain reaction that produces, in exponential quantities, a specific DNA sequence, provided that the termini of the sequence are known in sufficient detail so that oligonucleotide primers can be synthesized which will hybridize to them, and that a portion of the sequence is available to initiate the chain reaction. One primer is complementary to the negative strand, and the other is complementary to the positive strand. As applied to the instant invention, the primers employed are complementary to the 5' end of GAP 6, and are complementary to and flank the EcoRI sites of lambda gt11, or lambda gt10. Because the orientation of a particular cDNA insert in either vector is not known, it was necessary to run separate reactions with oligonucleotides that flank both sides of the EcoRI site. Exemplary of primers usable with lambda gt11 are two 24-base sequencing primers, 1218 and 1222, produced by New England Biolabs. Similarly, primers compatible with lambda gt10 are also available from New England Biolabs, and these are 1231 and 1232. Thus, separate reactions were run with either 1218, 1219, or 1231 and 1232, and the appropriate GAP 6 primer.

The primers are annealed to denatured DNA, followed by extension with a suitable DNA polymerase enzyme, such as the large fragment of DNA polymerase I (Klenow), or preferably a DNA polymerase that is stable in the presence of detergents and nucleotides, which results in newly synthesized plus and minus strands containing the target sequence. Alernatively, a thermostable enzyme may be used which is present in thermostable bacteria. The enzyme may he produced using DNA recombinant techniques as described in U.S. Patent application Ser. No. 063,509 now U.S. Pat. No. 4,889,818, filed Jul. 17, 1987. Because the newly synthesized sequences are also templates for the primers, repeated cycles of denaturing, primer annealing and extension results in exponential accumulation of the region defined by the primer. PCR thus produces discrete nucleic acid duplexes of cDNA inserts having termini corresponding to the ends of the specific primers employed.

Although PCR can be performed using a variety of reaction conditions, as described in the references presented above, the preferred reaction conditions are as follows. Plaques that hybridize to a particular probe are eluted into either 0.5 ml of water, or SM buffer, and 50 μl of the eluate combined with 10 μl of 10×PCR buffer, 1.5 μl of 10 mM dNTP's, 1 μl of a first and second primer, each at a quantity of about 20 pmoles, 0.2 μl of Taq polymerase equivalent to 1 unit of activity. The final volume is 100 μl. PCR 10×buffer consists of 500 mM KCl, 200 mM Tris-HCl, pH 8.4, 25 mM $MgCl_2$ and 1 mg/ml.

GAP encoding sequences: Gap 6 DNA was sequenced, and an oligonucleotide probe based on the sequence, GW50, synthesized, radiolabelled, and used to rescreen the Clontech lambda gt11 library, and to screen a second cDNA library made from K562 cells. K562 cDNA was cloned in lambda gt10, and a description of this library is presented by Mes-Masson et al., 1986, in the *Proceedings of the National Academy of Sciences*, 83, 9768. This publication is hereby incorporated by reference in its entirety. The oligonucleotide, GW50, has the following sequence:

5' TTTAAATTCACTGTACTCTTCTTCTGGCATGAT 3'

Hybridization of GW50 to either library was conducted as described above with the exception that the washing steps after the hybridization were more stringent. Specifically, the filters containing plaques were washed twice, for 15 minutes each wash, with 2×SSC containing 0.1% SDS at room temperature and then two additional washes, for 15 minutes each, with 0.2×SSC containing 0.1% sodium dodecyl sulfate at 55° C. Autoradiography of the filters prepared from the Clontech library revealed 160 positive plaques, while only one plaque was detected from the K562 library.

Using the sequence of GAP 6, DNA primers, LC121 and LC122, with sequences complementary to the 5' region of GAP 6, were synthesized.

LC121 5' GAGGAAGATCATCAAAGACAAACTCT 3'

LC122 5' TCTGTAATCGGCTCAACTGGCAGCG 3'

LC121 corresponds to the 5' end of GAP 6 in the anti-sense direction.

The 163 positive plaques from the Clontech library, and the one positive plaque from the K562 library, were removed from agarose plates using a Pasteur pipette, and eluted into 0.5 ml of SM buffer for 30 minutes. Each isolate was then PCR processed as described above using LC121 in combination with the appropriate lambda primers. Typically, a denaturation step was run for 2 minutes at 94° C., followed by an annealing step for 30 seconds at 55° C., and an extension step for 5 minutes at 72° C. The reaction was most often run for 30 cycles. The resulting amplified cDNA inserts were sequenced.

Sequencing can be performed using the techniques referred to above, or by direct sequencing of single stranded DNA produced by PCR. The use of PCR to generate single stranded DNA is described in a co-pending U.S. patent application, Ser. No. 248,896, titled "Method for Generating Single Stranded DNA by the Polymerase Chain Reaction", Filed on Sep. 23, 1988. This patent application is hereby incorporated by reference in its entirety.

Typically about 50 μl of the PCR reaction was separated on a 1% agarose TAE gel, the region of the gel containing the amplified products excised, and the PCR products extracted from the agarose and suspended in about 10 μl–20 μl of TE buffer. Generally about one tenth of this volume was subjected to asymmetric PCR amplification. The reaction conditions employed are described in the above cited patent application. The primers were typically used in a ratio of about 100:1, or about 50:0.5 pmoles.

Using LC121, 14 of the 163 lambda gt11 plaques were found to have an additional 320, or greater number of base pairs 5' of GAP 6, while the single plaque isolated from the K562 lambda gt10 library, referred to as K16, was determined to have a cDNA insert consisting of GAP 6 plus an additional 700 base pairs 5' thereto. Based on the latter sequence, several additional oligonucleotides, LC136, LC138, and LC140 were synthesized and used in conjunction with LC121 to again screen the 163 plaques from the Clontech library. The primers have the following sequences:

```
LC1365'  CGTAAATTGCAAAATGCCTGCAGACCTTG 3'
LC1385'  GTTTTCCTTTGCCCTTTTTCAGAAGATAAC 3'
LC1405'  TGTCATTGAGTACTTGTTCTTGATCCTGC 3'
```

Figure 5A:
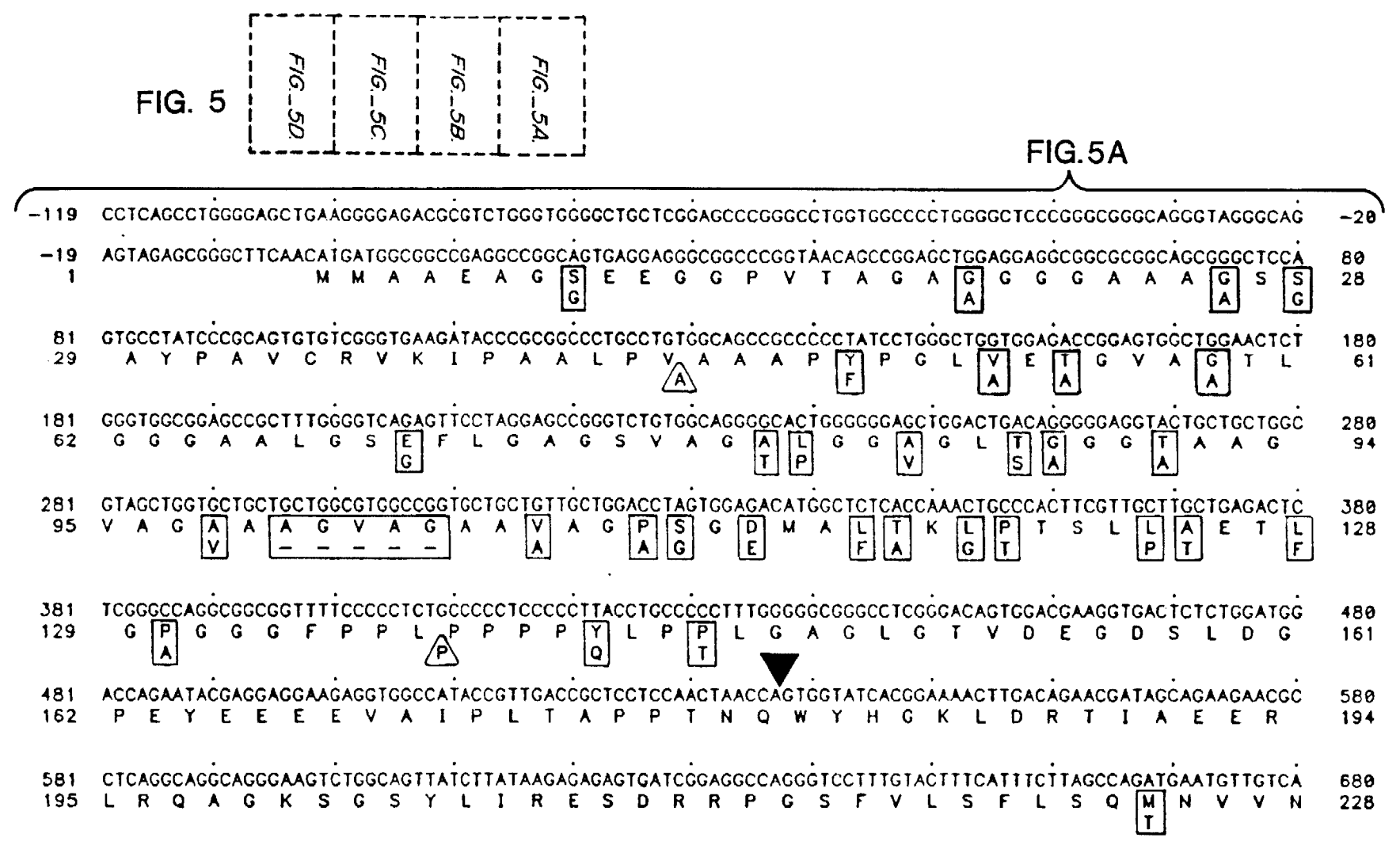

Rescreening the 163 plaques with LC136 revealed that 82 plaques were positive, while rescreening with LC138 plus LC140, revealed that 63 of the plaques were positive. Of the 63 positive plaques, 38 were subjected to PCR using the primers 1218 and LC138; and 1222 and LC138. Of these, six were found to have long stretches of DNA 5' to GAP6. Sequencing in M13m18 revealed that they represent different length fragments of the same type of transcript. Two of the clones were studied in detail, clone 7 and clone 101. Clone 101 contained sufficient DNA to encode a protein of 1047 amino acids, which would have a molecular weight of 116,000 daltons. This is similar to the molecular weight of the GAP protein purified from human placenta as described above. Thus, clone 101 contains the full length GAP cDNA. Clone 101 was sequenced, and the sequence is shown in FIG. 5. Clone 7 was also sequenced, and shown to have the identical sequence as clone 101 but lacking 33 base pairs from the 5' end.

Figure 6:
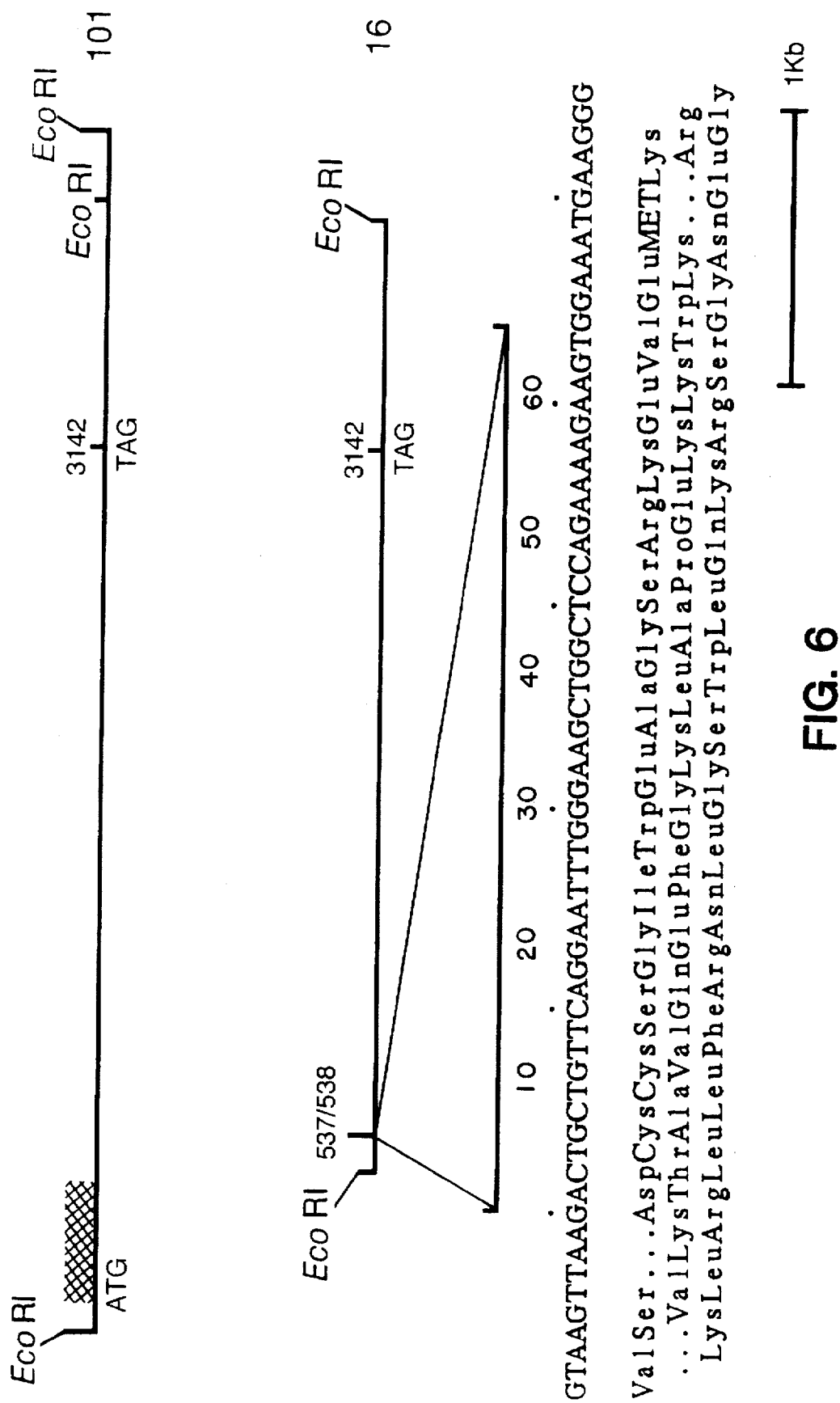
FIG. 6 presents the structural relationship between lambda clones, clone 101 and clone 16.

In addition to the above, two plaques were identified from the 163 plaques initially determined to be positive with GW50 that contained cDNA inserts consisting of an additional 65 base pairs inserted between nucleotides 537 and 538 of clone 101. One of the two clones, clone 16, lacks the first 180 amino acids of clone 101, while the other clone, clone "Sleepy", lacks at least the first 180 amino acids, and additionally has a truncated 3' end at about base 2448 of clone 101. The DNA sequence of the 65 base pair insert is shown in FIG. 6 for clone 16.

7. Expression of GAP

Figure 7A:
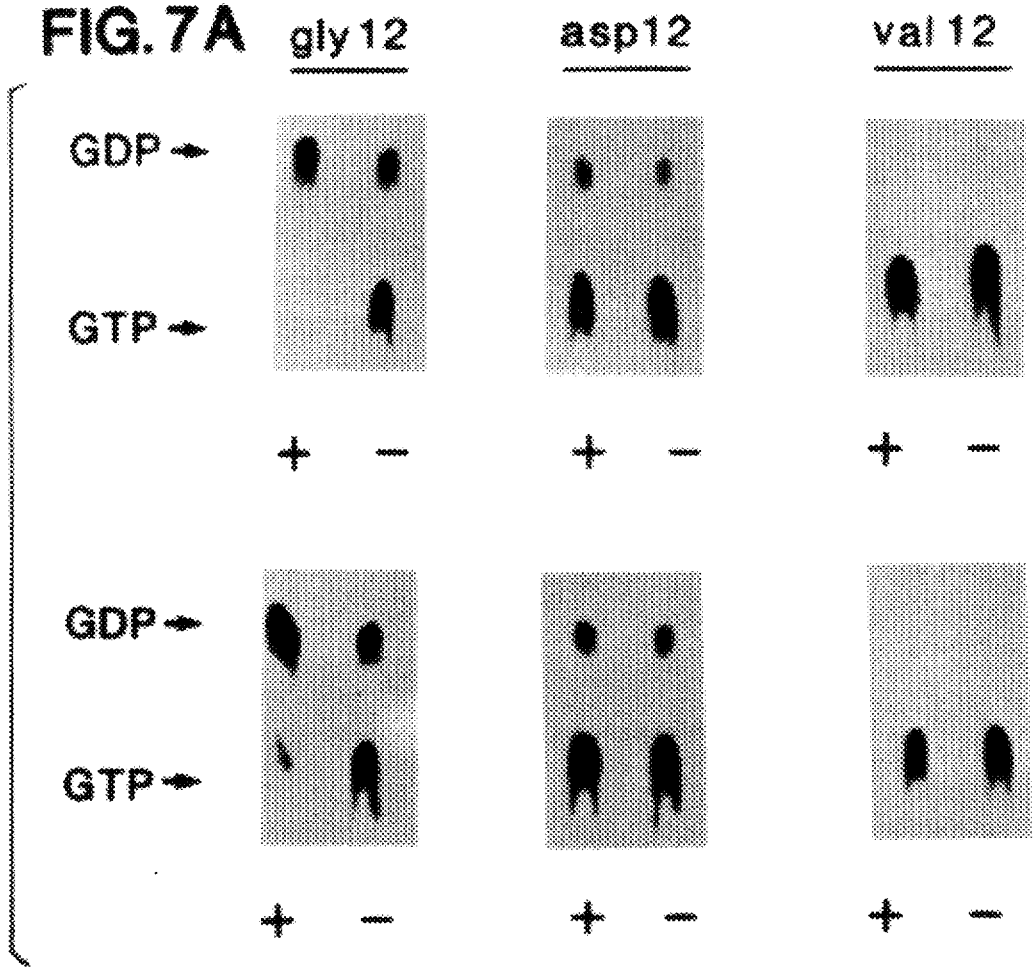
FIGS. 7A and 7B depict the result of GAP assays conducted in the presence of lysates prepared from lambda lysogens of clones 7 (FIG. 7A, top section) and 101 (FIG. 7A, bottom section); and of Sf9 cell lysates transfected with pAcC12-GAP 5 (FIG. 7B).
Figure 7B:
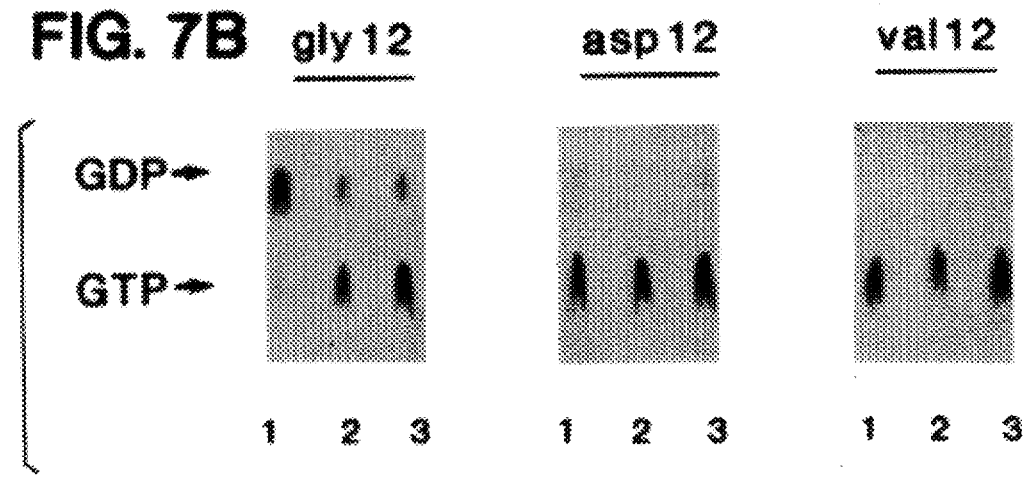

Lambda lysogens: GAP activity was detected from lysates of lambda lysogens of clones 7, 16, and 101. Lysogens were generated in *E. coli* strain Y1089. The procedures for growing, inducing, harvesting, and lysing the cells is described in T. Huynh et al., in "DNA Cloning Techniques: A Practical Approach", D. Glover, Ed. (IRL press, Oxford, 1985) pp 49–78. This publication is hereby incorporated by reference in its entirety. Briefly, supernatants obtained from lysates were dialyzed into GAP assay buffer consisting of 20 mM Tris-HCl, pH 7.0, 1 mM $MgCl_2$, 0.1 mM DTT, 0.1% NP40, 100 μM PMSF, and GAP activity measured using the TLC-based GTPase assay described above. 2.2 μM of either normal N-ras p21 protein having glycine at position 12, or mutant p21 proteins wherein glycine is substituted with aspartic acid or valine, were incubated with 0.25 μM [$\alpha$-$^{32}$P] GTP (800 Ci/mmole) for 15 minutes at 37° C. in the presence or absence of lambda lysate. As discussed earlier, the mutant p21 proteins have transforming activity and do not exhibit significant GAP stimulatable GTPase activity. About 10 μl of lysate or GAP assay buffer was added, and after 1 hour at room temperature, p21 was immunoprecipitated and associated nucleotides analyzed by chromatography on PEI cellulose in 1M LiCl. An additional control was run for GAP activity; it consisted of testing an irrelevant lysogen lysate, specifically lambda gt11 lacking a cDNA insert. The results are shown in FIGS. 7A–7B for clones 7 and 101. The upper part of FIG. 7A. Shows the results for clone 7, while the lower region of the panel shows the results for clone 101. It is apparent that lysates from both clones stimulate the hydrolysis of GTP to GDP in the presence of normal p21, but not in the presence of mutant p21 proteins. Moreover, when GAP buffer is substituted for normal p21, or the mutants, there was no effect on GTP hydrolysis. The irrelevant lysogen lysate also did not support GTP hydrolysis.

Transfection of *Spodoptera frugiperda*: The full length cDNA insert in clone 101 was expressed in insect cerls, *Spodoptera frugiperda*. The insect cell line, Sf9, was transfected with a baculovirus expression vector, pAcC12, containing the GAP encoding EcoRI fragment of clone 101, and GAP activity measured in cell extracts.

Figure 8:
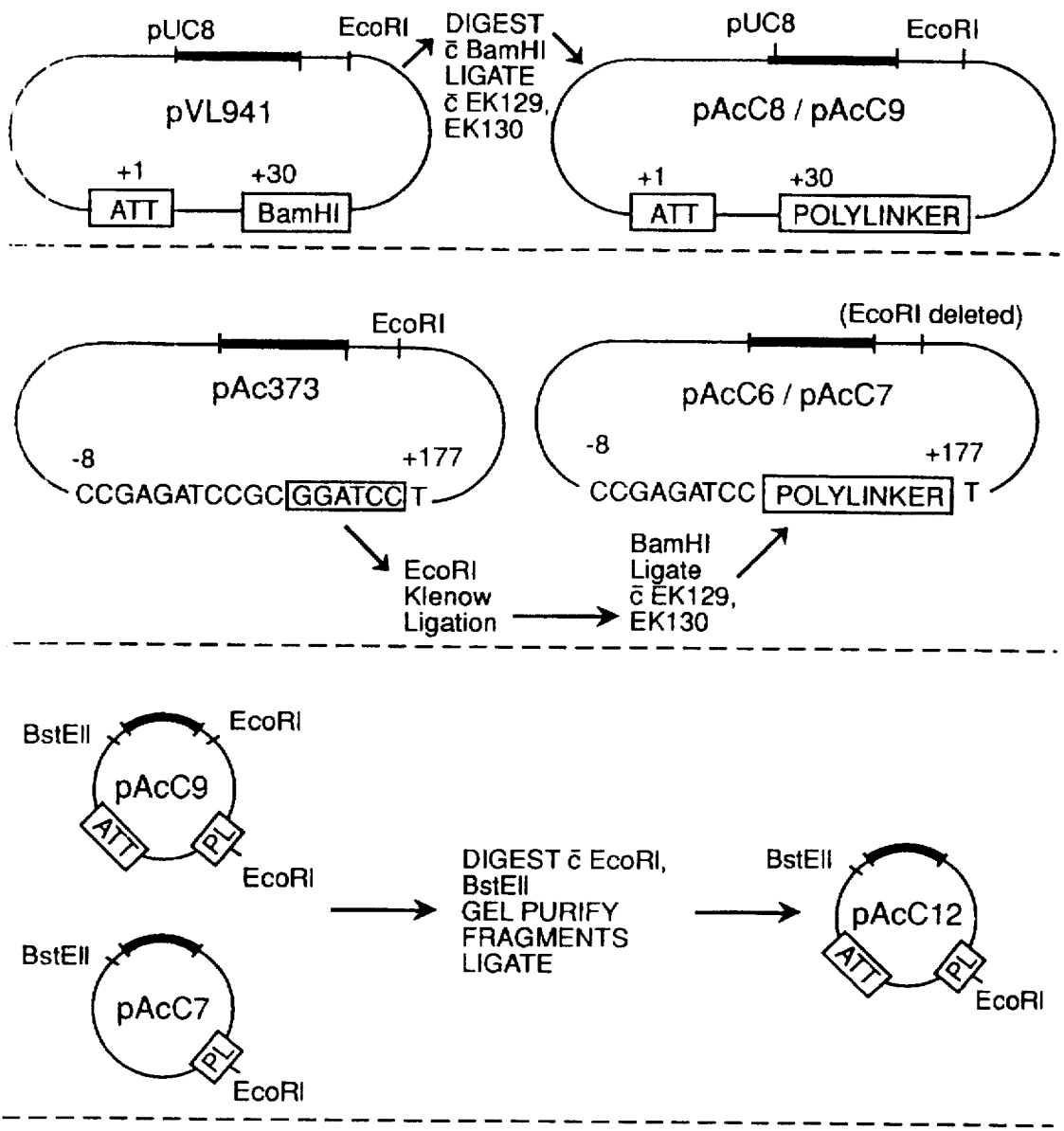
FIG. 8 shows the construction of pAcC12.
Figure 12:
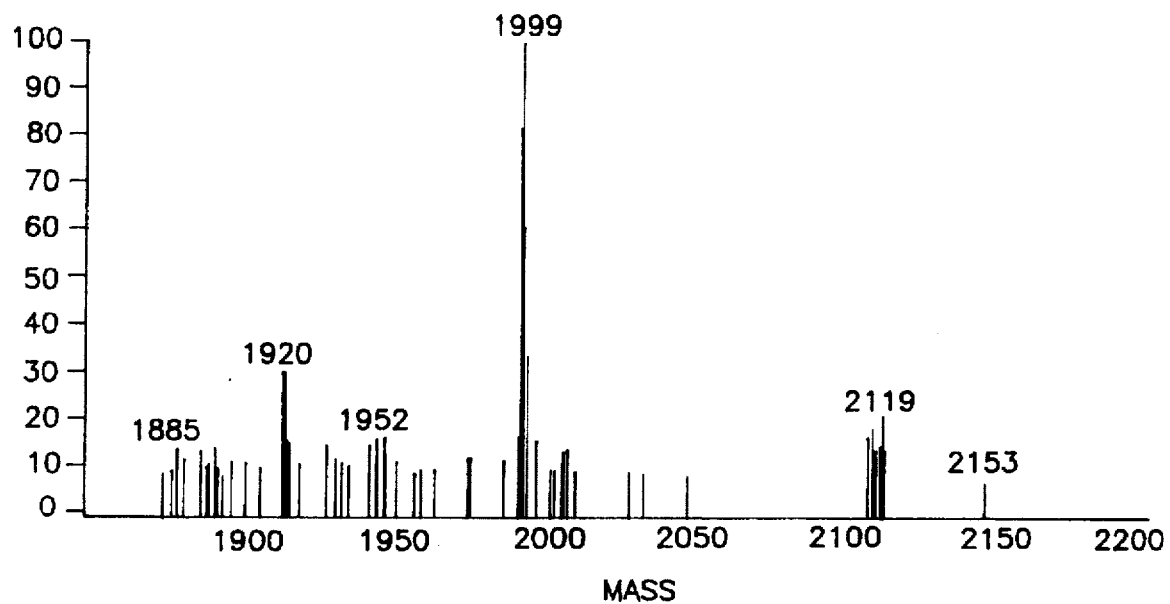
FIG. 12 presents the mass spectrometer analysis of cGAP 13.

The baculovirus vector, pAcC12, was constructed from preexisting vectors, particularly pAc311 and pAc373, as described by Luckow and Summers in *Biotechnology*, Vol. 6, p. 47 (1988); U.S. Pat. No. 4,745,051; and EPA 127,839. Additional details are presented by Summers and Smith in "A Manual of Methods for Baculovirus Vectors and Insect Cell Culture Procedures", Texas Agricultuaal Experiment Station Bulletin No. 1555, May, 1987. All of these references are hereby incorporated in their entirety.

pAcC12 was constructed as described below, and as shown in FIG. 8. The transfer vector pAc311 was site-directed mutagenized using M13 mutagenesis techniques to convert the polyhedron gene initiation codon, ATG, to ATT. The resulting vector was designated pVL941, and is described in detail by Luckow and Summers in *Virology*, 170(1):31 (1989) titled "High Level of Expression of Non-Fused Foreign Genes with Autographa Californica Nuclear Polyhedrosis Virus Expression Vectors". A polylinker was inserted into pVL941 at a unique BamHI site 30 base pairs downstream of the ATT sequence. pVL941 was digested with BamHI, and the polylinker, consisting of two complementary self-annealed oligomers, EK 129 and EK130, having the sequences shown below, ligated to produce the vectors pAcC8 and pAcC9 that carry the polylinker in different orientations. The polylinker has a restriction site for EcoRI, as well as for other restriction enzymes.

EK 129:
5'GATCCACCATGGAGCTCGAGATCTAGAATTCTGCAGCCCGGGTACCGATC 3'

EK 130:
5'GATCGGTACCCGGGCTGCAGAATTCTAGATCTCGAGCTCCATGGTGGATC 3'

Because pAcC8 and pAcC9 have two EcoRI restriction sites, one in the polylinker and the other in the plasmid DNA as shown in FIG. 8, it was desirable to remove the plasmid EcoRI site so that the Gap EcoRI encoding fragment of clone 101 could be inserted into the polylinker site. This was achieved using the transfer vector pAc373. pAc373 is similar to pAc311 except that the nucleotide sequences spanning the polyhedron start codon differ. Thus, the EcoRI site was itnived fkcm pAc373 by digesting the vector to completion with EcoRI, and the ends made blunt using the Klenow fragment under the appropriate reaction conditions. Following ligation and transformation into E. coli DH 5, colonies were identified that lacked the EcoRI site by restriction analysis of miniprep DNA.

pAc373 lacking the EcoRI site was further modified by incorporating the polylinker consisting of the oligomers, EK129 and EK130, shown above, by digesting the vector with BamHI, followed by ligating the oligomers. The resulting vectors, pAcC6 and pAcC7, contain the polylinker in different orientations.

The final construct, pAcC12, was generated from pAcC7 and pAcC9 as shown in FIG. 8. These vectors contain the polylinker in the same orientation. Both vectors were digested with Bst EII and EcoRI and the resulting fragments electrophoretically purified. The Bst EII/EcoRI fragment of pAcC7 containing the pUC 8 sequences, and partial polylinker sequences was ligated to the large BstEII/EcoRI fragment of pAcC9. This latter fragment contains the ATT sequence and the remaining polylinker sequences.

The transfer vector, pAcC12, has the EcoRI GAP fragment of clone 101 inserted in both orientations. The correct orientation was designated pAcC12 GAP 5, while the incorrect orientation was designated pAcC12GAP 101-7. About 2 μg of either plasmid was transfected into 2×10⁵ Sf9 cells, the cells grown for 4 days, isolated by centrifugation, and cell extracts made by solubilizing the cell pellet. The preferred solubilization solution consists of 0.5% NP40, 10 mM Tris HCl, pH 8.0, and 150 mM NaCl. The extract was centrifuged for 15 minutes at 15,000×g and aliquots diluted into GAP assay buffer, and assayed for GAP activity as described above. Methods for growing Sf9 cells are well known in the art, and detailed procedures for their cultivation can be found in M. Summers and G. Smith in "A Manual of Methods for Baculovirus Vectors and Insect Cell Culture Procedures", Texas Agricultural Experiment Station, Bulletin No. 1555 (May, 1987) or in EPO 127,839 to G. E. Smith and M. D. Summers. Preferred media and culturing conditions can be found in co-pending, commonly owned U.S. patent applications: Ser. No. 77,181, titled "Airlift Insect Cell Culture," filed Jul. 24, 1987, abandoned, continued-in-part in U.S. patent application Ser. No. 374, 004, filed Jun. 29, 1989, abandoned, continued-in-part in U.S. patent application Ser. No. 427,035, filed Oct. 24, 1989, abandoned, continued in U.S. patent application Ser. No. 830,513, filed Jan. 30, 1992; Ser. No. 77,303, now titled "Serum Free Media for the Growth of Insect Cells and Expression of Products Thereby," now U.S. Pat. No. 5,024, 947; and Ser. No. 77,189, titled "Lipid Microemulsions for Culture Media," filed Jul. 24, 1987, abandoned, continued-in-part in U.S. patent application Ser. No. 248,830, filed Sep. 23, 1988, abandoned, continued in U.S. patent application Ser. No. 829,610, filed Jan. 30, 1992. These publications and patent applications are hereby incorporated by reference. FIG. 7B shows the results. The effect of pAcGAP 5 and pAcGAP 101-7 are shown in lanes 1 and 2, respectively; lane 3 presents a buffer control. Note that pAcGAP 5 stimulates normal ras p21 GTPase activity, whereas it is without effect on the p21 mutants. In contrast, there is no stimulation of GTPase activity by pAcGAP 101-7 of either normal ras p21proteins or the mutants.

It is important to note that baculovirus can be recovered from Sf9 cells transfected with the above described transfer vectors using the techniques described by Summers and Smith, above. Such virus can be employed to transform cells directly with the appropriate GAP clone.

Synthesis of Peptide Sequences

To determine the GAP's active site for binding to the ras p21 protein, ras p21-GDP complex, or ras p21 -GTP complex, several fragments of clone 101 were synthesized and tested. Peptides may be synthesized by methods well known in the art. The preferred method of peptide synthesis is the solid-phase method, described in more detail in Merrifield R. B., (1985) Sci., 232:341–347, on a Biosearch 9500 automated peptide machine, cleaved with hydrogen fluoride, and purified by preparative HPLC using a Waters Delta Prep 3000 instrument, on a 15-20 μm Vydac C4 PrepPAK column. An alternative method is by means of ABI Automatic Synthesizer.

Thus, peptides corresponding to amino acids positions 876–890 (denoted peptide G65), 975–990 (denoted peptide G73), 891–906 (denoted peptide 891), and 890–906 (denoted peptide cgap 13) of the full length GAP were synthesized. (FIGS. 9A–9D show the locations of the peptide sequences; FIG. 10 tabulates the corresponding positions). These peptides were tested for their ability to affect ras p21 protein hydrolysis of GTP in the presence or absence of GAP. It was found that peptide 891 and cGAP 13 inhibit the stimulation of hydrolysis of GTP by p21, both in the presence and absence of GAP, while the other peptides had no effect on the reaction. Peptide 891 has the following amino acid sequence: MRTRVVSGFVFLRLIC. Except for an extra threonine at the beginning of the peptide, cGAP 13 has the same sequence as peptide 891. The cGAP 13 was purified using reverse-phase high performance liquid chromatography. The amino acid analysis of cGAP 13 is shown in FIG. 11. The mass spectrometer analysis of cGAP 12 is shown in FIG. 13. It is worth noting that there is a significant amount of methoxybenzyl present.

Figure 13A:
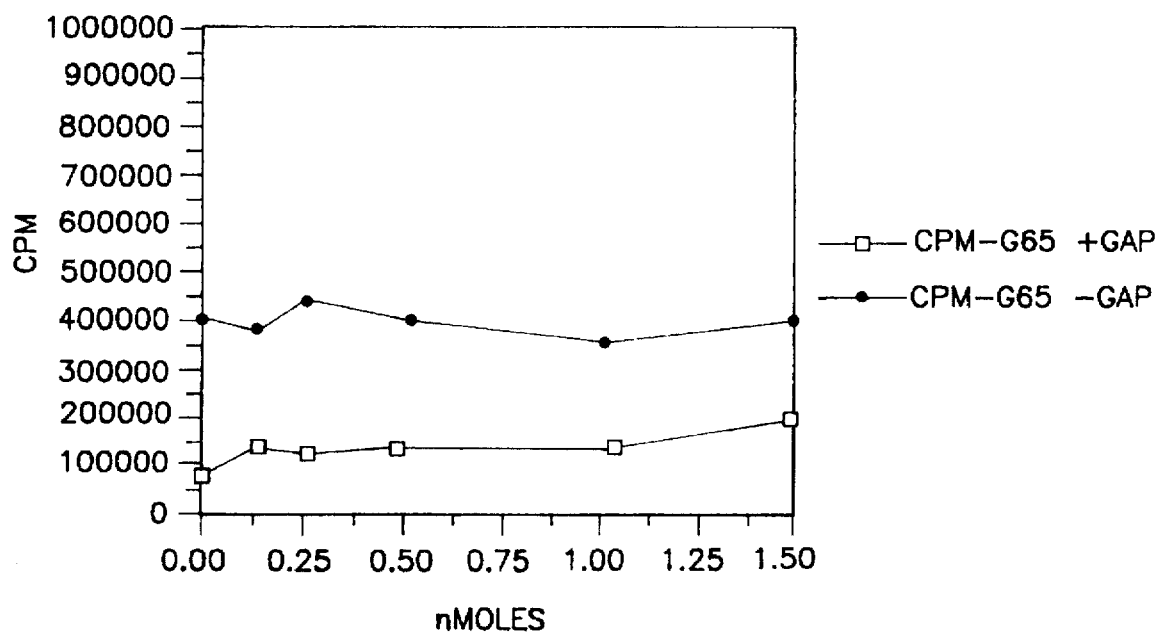
FIGS. 13A–13C show the graphs indicating the presence of radioactive p21-GTP complex and thus any effect peptides G65 (FIG. 13A), G73 (FIG. 13B), and peptide 891 (FIG. 13C), have on the p21 hydrolysis of GTP in the presence and absence of GAP.
Figure 13B:
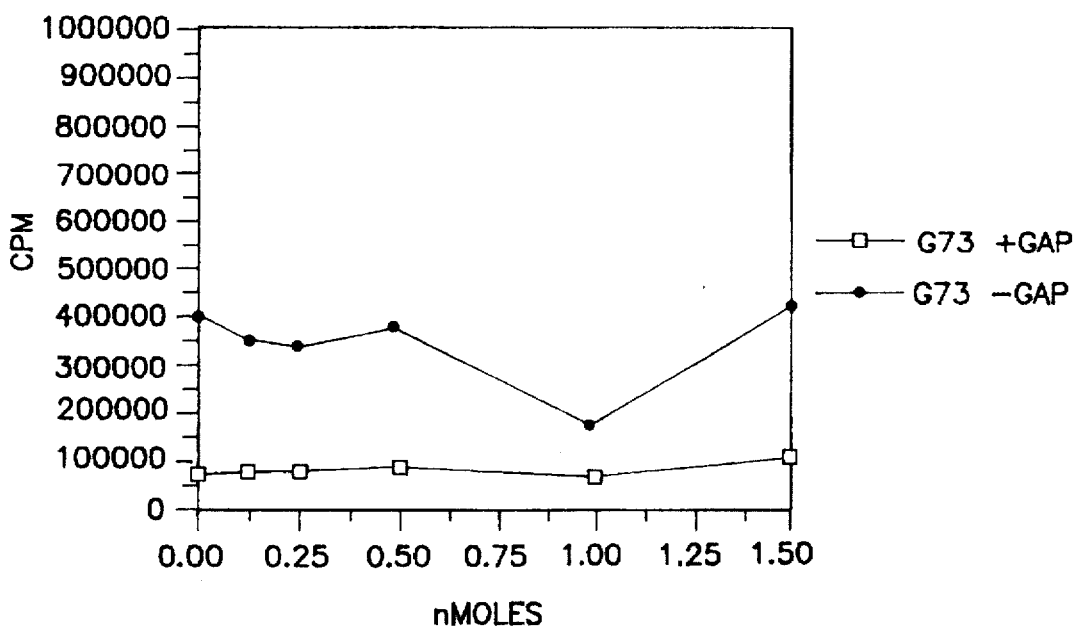
Figure 13C:
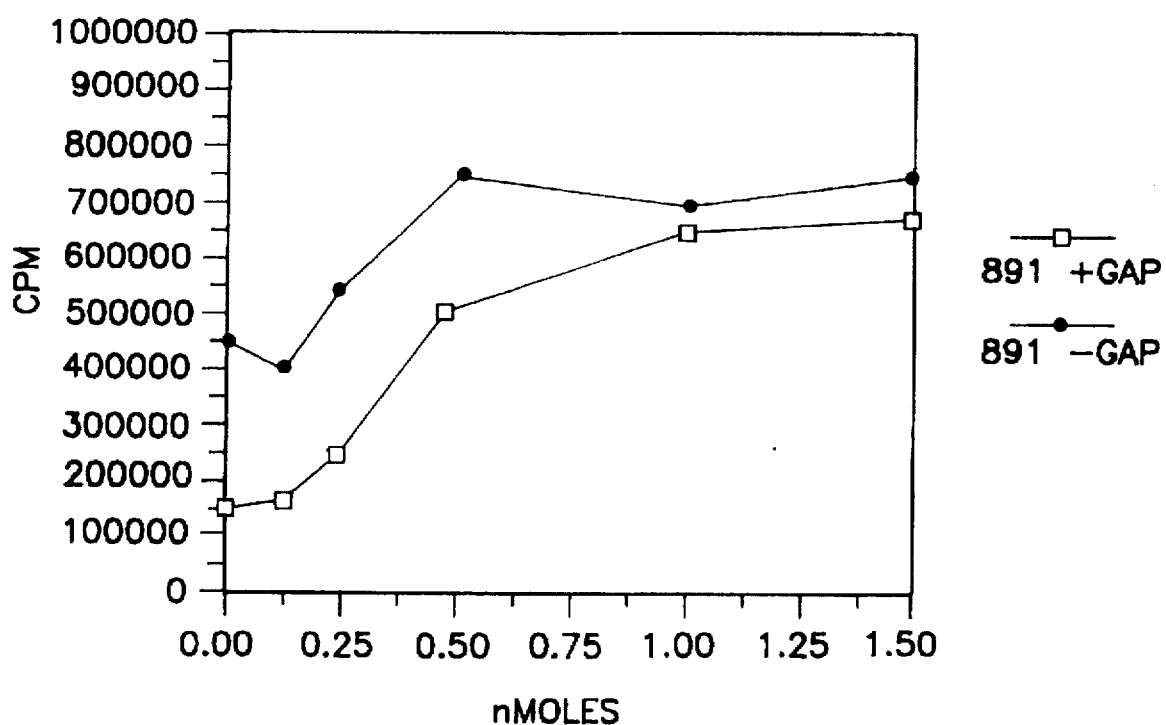

Determination of Peptide Sequences Capable of Inhibiting Hydrolysis of GTP bv Ras p21 Both in the Presence and Absence of GAP The above four peptides, in the following two experiments, were tested for their abilities to inhibit the hydrolysis of GTP by ras p21 protein, in the presence and absence of GAP. The first experiment involved peptides G65, G73 and 891. It was carried out as follows: purified wild type ras p21 protein was incubated with 0.25 µM 32-P gamma-GTP in 100 mM NaPO$_4$, pH 6.8, 0.5 mM DTT, 0.5 mM EDTA, 0.005% Na cholate, and 0.5 mg/ml BSA for 15 minutes at 30° C. The mixture was then diluted ten fold with TNM buffer (comprising 20 mM Tris-HCl, pH 7.0, 100 mM NaCl, 5 mM MgCl$_2$). 20 µl (0.05 µg of p21) of this mixture was then combined with 2 µl of the peptide in 25 mM NaOAc, pH 5.5 and incubated for 5 minutes at room temperature. The GAP assay was initiated by the addition of 12 ng GAP in 5 µl TNM buffer with 1 mg/ml BSA or 5 µl TNM BSA buffer for the GAP independent reactions, and the resulting mixture was incubated for 30 minutes at room temperature. The samples were then filtered through nitrocellulose membranes and washed three times with cold TNM. The filters were dried and their radioactivity counted. Graphs based on the data are shown in FIG. 13A-13C. The y-axis in the charts indicate radioactive counts per minute for the radioactive ras p21-GTP complex. The x-axis indicate the amount of peptides added in nmoles. The first chart serves as a control. In the presence of GAP, the radioactive ras p21-GTP complex is hydrolyzed to GDP and ras p21 protein, thus reducing the resulting amount of radioactive p21-GTP bound to the filter and consequently, the radioactive counts detected. In the absence of GAP, the radioactive counts remained relatively high because of the lack of GAP stimulated hydrolysis. It is important to note, as shown in FIG. 13, that even in the absence of GAP, the peptide alone significantly inhibits ras p21 protein hydrolysis of GTP. The charts show that peptides G65 and G75 do not affect the hydrolysis of GTP. However, peptide 891 adversely affects the hydrolysis of GTP.

Another experiment comparing the efficacy of cGAP 13 and peptide 891 in preventing the hydolysis of GTP was carried out as follows. The assay measured the ratio of GDP formed resulting from the hydrolysis of GTP to the remaining GTP in the assay solution. Peptides 891, cGAP 13, and G65 were separately tested in the presence and absence of GAP. Peptide G65, which served as a control, and α-32-P-GTP were used.

The assay was carried out as follows. The p21-GTP was diluted at a ratio of 1 to 10 in an assay buffer consisting of TNM at pH 7.0, 1mM DTT, and 100 µM GTP. A mixture consisting of 20 λ of p21 at 0.25 µM, and 2 λ of the peptide (in TNM, 1mM DTT and 100 µM GTP) was prepared. To this mixture was added 5 λ, i.e. 12ng of GAP diluted in TNM and 1 mg/ml BSA; for experiments without GAP, 5 λ TNM/BSA were added instead. The resulting mixture was incubated for 30 minutes at room temperature. The reaction was stopped and the nucleotides were eluted from ras p21 protein with 2% SDS, 40 mM EDTA at 65° C. for 5 minutes. The nucleotides were chromatographed on PEI Cellulose in 1M LiCl. GTP and GDP spots were visualized with autoradiography and identified by means of standard solutions. The individual spots from the PEI cellulose plates were scraped and the radioactivity counted.

Figure 14A:
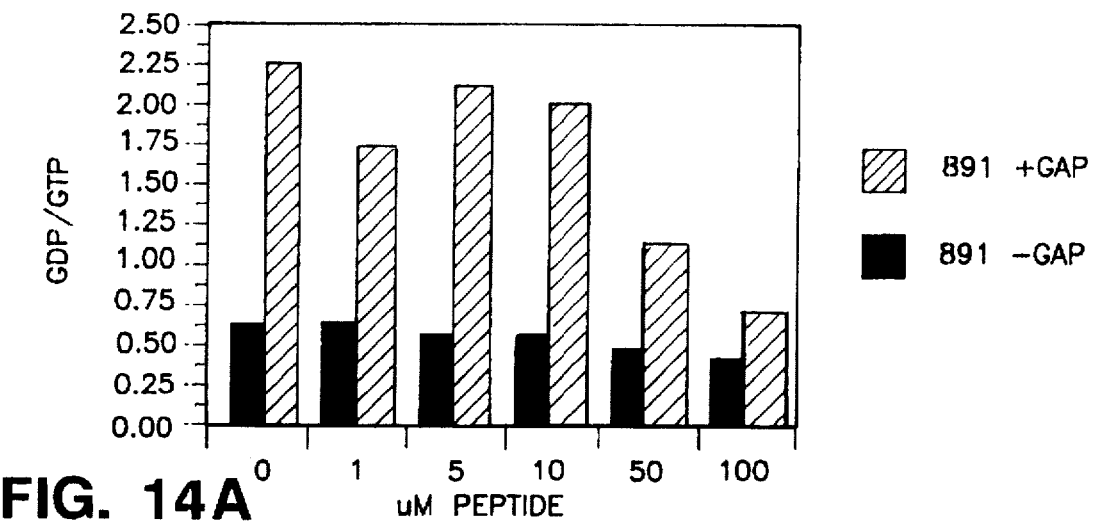
FIGS. 14A–14C present the bar charts showing the ratio of the radioactive counts of GDP over GTP in experiments involving G65(FIG. 14C), cGAP 13(FIG. 14B), and peptide 891(FIG. 14A), in the presence and absence of GAP.
Figure 14B:
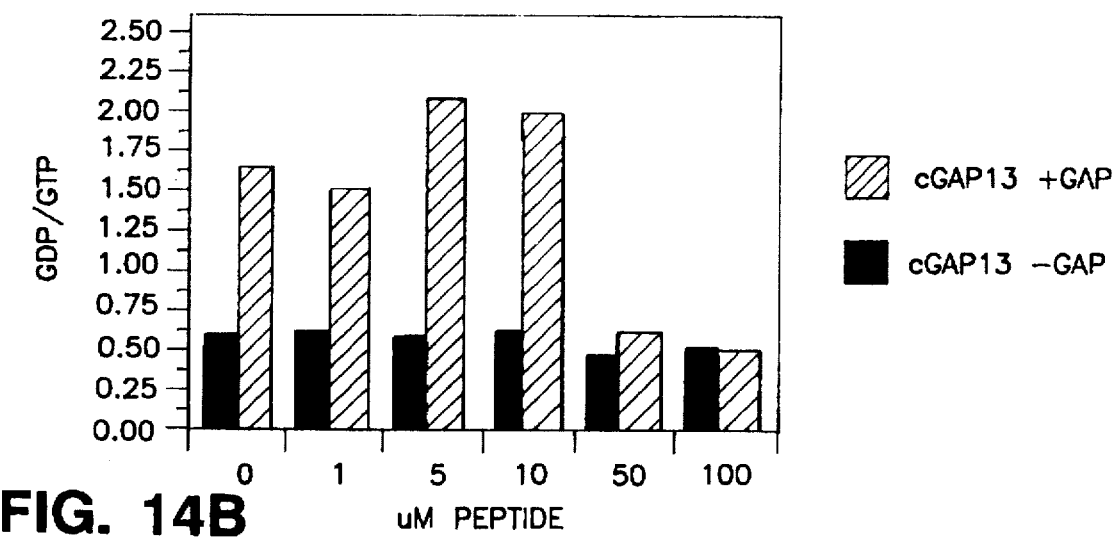
Figure 14C:
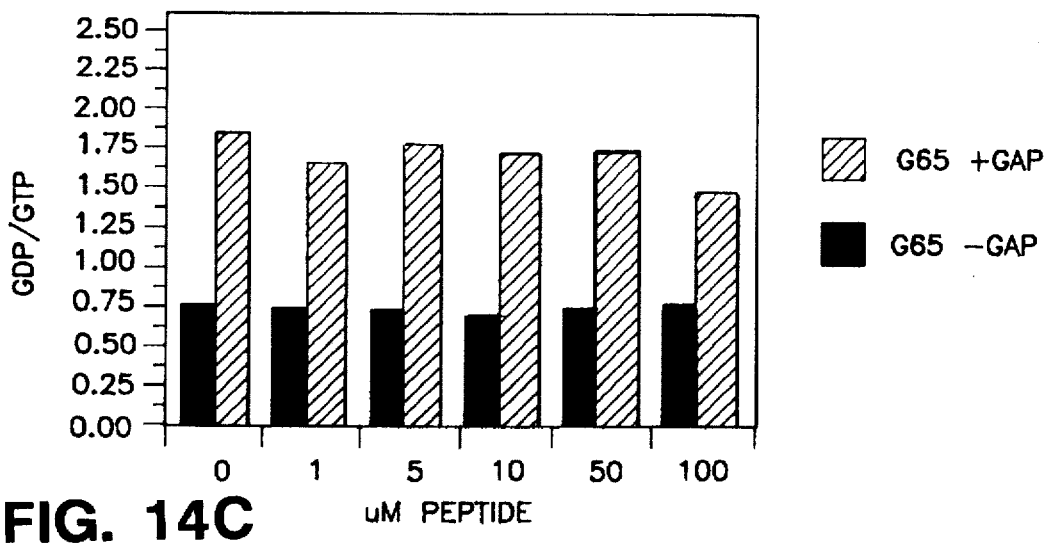

The ratio of radioactive counts of GDP over GTP was plotted on bar charts (FIGS. 14A-14C) which shows that at a concentration of 50 to 100 µM and above, both peptide 891 and cGAP 13 clearly inhibit the hydrolysis of p21-GTP and therefore the production of GDP. Marginal inhibition was observed at 10 µM concentrations of the peptides. The above inhibitory effects were observed in the presence of GAP. Absent GAP, there is a small but significant change in the amount of GDP formed over the range of peptide concentrations used. G65, the control, exhibits no inhibitory effect on p21-GTP hydrolysis in the presence of GAP.

Peptide Mediated Dissociation of GDP From ras p21-GDP Complex

Peptides 891 and cGAP 13 mediate the dissociation of GDP from ras p21-GDP complex, but not the dissociation of a non-hydrolyzable analog of GTP, GTPγS, from ras p21-GTPγS complex. The following experiments confirmed the above. The control used was mastoporan (MP). MP has the following sequence: INLKALAALAKKIL-NH$_2$. MP was chosen as a control for two reasons. First, like peptide 891, MP was a peptide with four positive charges. Second, MP had been shown to affect a different class of guanine nucleotidebinding proteins, i.e. the GTP-binding regulatory proteins (G proteins). MP mediates the dissociation of GDP from the G proteins. Higashijima, T. et al., 1988, *J. of Biol. Chem.*, 263:6491-6494, entitled, "Mastoparan, a Peptide Toxin from Wasp Venom, Mimics Receptors by Activating GTP-binding Regulatory Proteins (G Proteins)".

The experiment was carried out as follows: N-ras, a member of the ras p21 family, was incubated in 20 mM Tris 7.5, 0.5 mM DTT, 0.1% NP40, 1mM EDTA with 500 nM unlabeled GDP and 10 nM [α-$^{32}$P] GDP at 30° C. for 30 minutes. The MgCl$_2$ concentration was then adjusted to 5 mM. Unlabelled GDP (100 µM) was added and the incubation was continued in 20 mM Tris 7.5, 0.5 mM DTT, 0.1% NP40, 5 mM MgCl$_2$ with the following peptides respectively: 10 µM and 50 µM of 891 peptide, 10 µM and 50 µM of MP. No peptide was added to the control medium. At the indicated time points, 10 µl aliquots (0.5 pmoles) wete assayed for bound [α-$^{32}$P] GDP by filtration onto nitrocellulose filters using wash buffer containing 20 mM Tris 7.5, 100 mM NaCl, and 5 mM MgCl$_2$. The results are shown in FIG. 15.

Figure 15:
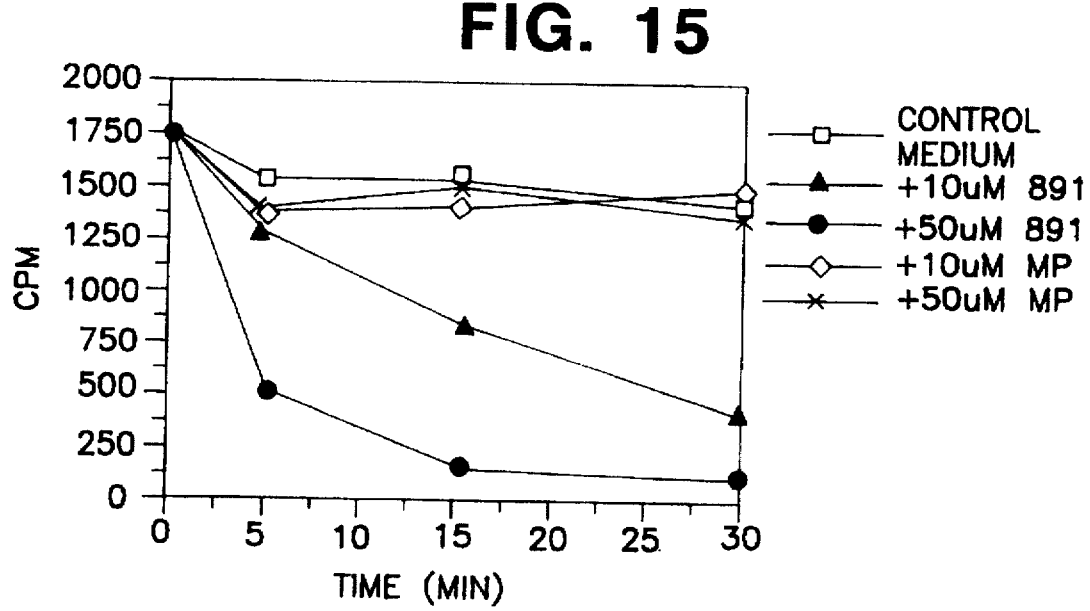
FIG. 15 presents the result of experiments showing peptide 891 causes dissociation of GDP from ras p21-GDP complex.

As shown in FIG. 15, the squares indicate the control medium without any added peptide. After the initial 5 minutes, the radioactive counts of the bound [α-$^{32}$P] GDP in the control medium were almost constant. The radioactive counts of the media containing MP, at the two concentrations tested closely followed that of the control media. Thus, MP had relatively no effect on the dissociation of the bound [α-$^{32}$P] GDP. In contrast, in the presence of pepiide 891, the bound [α-$^{32}$P] GDP decreased over time. An increase in the concentration of peptide 891 from 10 µM to 50 µM caused an increase in the rate and amount of GDP dissociated.

The above experiment was conducted using cGAP 13 which yielded similar results. Additionally, the same experiment using H-ras, another member of the ras p21 family also yielded a similar result for both peptides 891 and cGAP 13.

Figure 16:
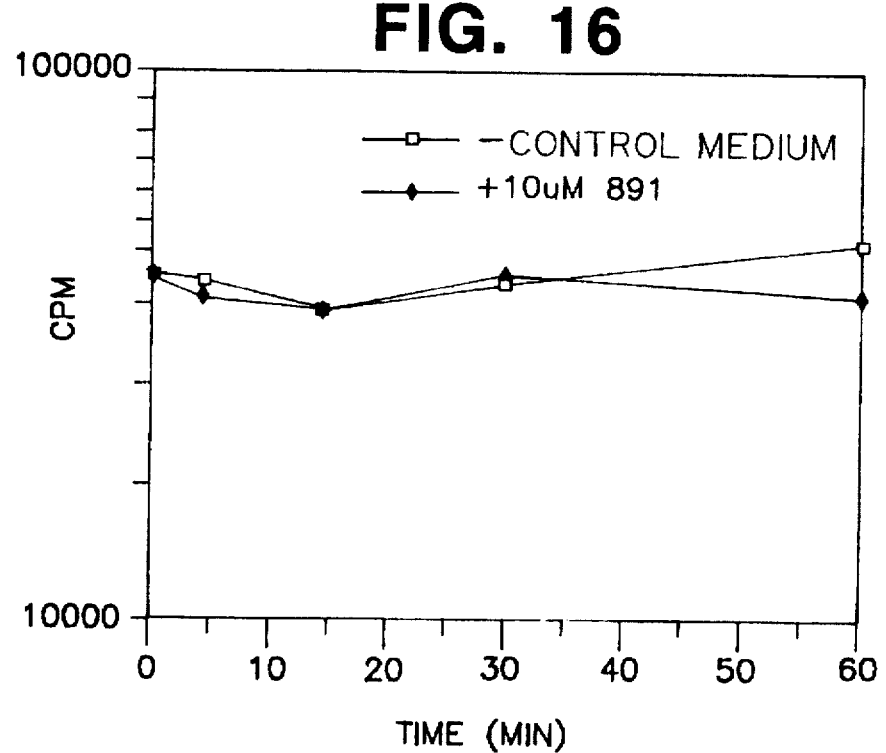
FIG. 16 presents the result of experiments showing peptide 891 does not cause the dissociation of GTPγS from ras p21-GTPγS.

Further, the above experiment was repeated using peptides 891 and ras p21-GTPγS. The result is shown in FIG. 16. The squares indicate the control medium without any added peptide. The radioactive counts of the control medium closely followed that of peptide 891. The result thus showed that peptide 891 does not cause dissociation of GTPγS from ras p21GTPγS.

Diagnostic Uses of Peptide Sequences

The peptides described herein may be employed in assaying for the presence of ras p21 protein, especially in tumors with an over expression of normal or oncogenic ras p21 protein. The availability of large amounts of these peptides will thus be a valuable addition to present cancer diagnostic methods. It will be appreciated by those skilled in the art that any fragments of peptide 891 or cGAP 13 which retain the ability for binding to the ras p21 protein or ras p21-GTP complex; and any peptide which competes with peptide 891 or cGAP 13 for binding to ras p21 protein or ras p21-GTP complex would be useful in the following described assay.

For example, ras p21 protein was assayed by means of peptides 891 and cGAP 13 in the following manner. First, labelled ras p21-GTP protein was prepared by incubating a 10 µM solution of ras p21 protein in 20 mM Tris, pH 7.5, 1 mM dithiothreitol, 0.1M NaCl, 0.1% NP40, 1 mM EDTA containing 1 µM GTP$\gamma$S$^{35}$(1350 Ci/mmole) for 30 minutes at 30° C.

The synthetic peptide was immobilized on nitrocellulose filters by pipetting 10 µl of a 1 mM solution (25 mM Na acetate, pH 5.5) of the peptide onto the filter using vacuum filtration. The filters were preincubated in a blocking buffer containing 20 mM Tris, pH 7.5, 0.1% bovine serum albumin, 0.1% ovalbumin and 0.05% Tween 20 for 30 minutes at room temperature. The filters were then transferred to 100 µl of 20 mM Tris at pH 7.5, 0.1% NP40, 5 mM MgCl$_2$. To the filters were added various concentrations, between 1 and 100 µM, of the free peptide and 1 µl of the ras p21-GTP$\gamma$S$^{35}$ preparation. Following a 30 minute incubation at room terature, the buffer was removed and the filters are washed three times with 1ml each of ice cold 20 mM Tris, pH 7.5, containing 5 mM MgCl$_2$. The filters were dried and the radioactive count per minute (CPM) was determined by scintillation counting. It will be appreciated by those skilled in the art that other assaying methods can be used. For example, the ras p21 protein may be labelled with an enzyme or a fluorogenic material and examined by enzymatic or fluorometric means.

Antibodies to the Peptides

Antibodies to peptides cGAP 13 and 891 are produced using standard procedures known in the arts. We hereby incorporate by reference U.S. Pat. No. 4,762,706, issued Aug. 9, 1988, to McCormick, et al. For example, antibodies are produced by injecting a host animal such as rabbit, rat, goat, mouse, etc., with the peptide or peptide fragment. Before injection, the peptides are first conjugated with keyhole limpet hemocyanin (KLH) or bovine serum albumin (BSA). The conjugation is achieved via the sulfhydryl group in the cysteine residue. A heterobifunctional crosslinking reagent, N-maleimido-6-amino caproyl ester of 1-hydroxy-2-nitro-benzene-4-sulfonic acid sodium salt,was prepared by the following procedure.

One molar equivalent (2.24 g) of 4-hydroxy-3-nitrobenzene sulfonic acid sodium salt (HNSA) was mixed together with one molar equivalent (2.06 g) of dicyclohexylcarbodiimide and one molar equivalent (2.10 g) of N-maleimido-6-aminocaproic acid in 25 ml of dimethylformamide (DMF) at room temperature overnight. A white precipitate of dicyclohexyl urea was formed. The precipitate was filtered and 300 ml diethyl ether is added to the mother liquor. After about 10 minutes to 4 hours a gummy solid precipitated from the mother liquor was formed. This solid was found to contain 58% of active HNSA ester and 42% of free HNSA.

The analysis consisted of dissolving a small amount of the precipitate in phosphate buffer at pH 7.0 and measuring absorbance at 406 nm; this reading provides the amount of unreacted free HNSA which is the contaminating material in the HNSA ester preparation. Addition of very small amounts of concentrated strong base (such as 5N NaOH) instantly hydrolyzed the ester formed and a second reading was taken. Subtraction of the first reading from the second yielded the amount of ester in the original material. The solid was then dissolved in DMF and placed on a LH20 Sephadex column and eluted with DMF so that the ester was separated from the contaminating free HNSA. The progress of purification was monitored by thin layer chromatography using eluting solvents of chloroform, acetone and acetic acid (6:3:1 vol/vol). The product was positively identified as mal-sac HNSA ester by its reactivity with amine. The yield of the pure ester was estimated to be approximately 30% of theoretical; the purified material consisted of 99% ester.

The ester thus obtained was found to dissolve fully in water and was found to be stable in water for several hours, provided no nucleophiles were added. When placed in 1N ammonia the ester produced the corresponding amide with a portion hydrolyzed to free acid. The purified ester was found to be stable for extended periods when stored dessicated.

About 0.5 mg of the purified mal-sac HNSA ester was dissolved in 1 ml of distilled water. A 10 µl aliquot of this solution was diluted into 1 ml of 10 mM phosphate buffer at pH 7.0. The absorbance at 406 nm was used to calculate the concentration of free HNSA as described above. When 50 µl of 4.8N sodium hydroxide solution was added to the diluted aliquot of ester and mixed, the absorbance of the solution at 406 nm increased significantly, indicating that the hydroxide nucleophile rapidly hydrolyzed the ester to component acid and free HNSA anion.

The difference between the post-base and initial free HNSA concentration represents the concentration of ester. From the actual concentration of ester and protein amino groups the amount of ester to be added to the protein solution to achieve the desired degree of substitution can be calculated.

The purified HNSA ester was then reacted with BSA as follows (the reaction with KLH was similar to this procedure):

A total of 22 mg (20 µmoles) of BSA (of molecular weight 66,296) was dissolved in 2.0 ml of 0.1M phosphate buffer at pH 7.5 to yield a total amine concentration of 1.0×10$^{-2}$ moles per liter (assuming 59 lysines/BSA molecule) A calculated amount (11 mg, 2.35×10$^{-5}$ moles) of the above-prepared mal-sac HNSA ester (97.7% pure) in powder form was dissolved in 2.0 ml of BSA solution. The reaction was carried out at room temperature. Ten µl aliquots were removed from the solution at timed intervals and were each diluted into 1.0 ml of 0.01M phosphate buffer at pH 7.0. The spectrum of each diluted aliquot was recorded using a Hewlett-Packard spectrophotometer and the absorbance at 406 nm measured. A total of 50 µl of 4.8N NaOH was then added to each aliquot, each aliquot was mixed and its spectrum retaken and the absorbance at 406 nm measured. The results appear in Table 1.

TABLE 1

| | Without NaOH | | With NaOH | | | |
|---|---|---|---|---|---|---|
| Time (minutes) | Absorb. Peak at 406 nm | Concen. of HNSA (moles/l) | Absorb. Peak at 406 nm | Concen. of HNSA (moles/l) | Concen. of Ester (moles/l) | % Ester Remaining in Solution |
| 0 | 0.046 | $1.03 \times 10^{-5}$ | 0.648 | $1.66 \times 10^{-4}$ | $1.56 \times 10^{-4}$ | 94.0 |
| 5 | 0.095 | $2.44 \times 10^{-5}$ | 0.547 | $1.40 \times 10^{-4}$ | $1.16 \times 10^{-4}$ | 82.9 |
| 9 | 0.112 | $2.87 \times 10^{-5}$ | 0.516 | $1.32 \times 10^{-4}$ | $1.03 \times 10^{-4}$ | 78.3 |
| 14 | 0.147 | $3.77 \times 10^{-5}$ | 0.579 | $1.49 \times 10^{-4}$ | $1.11 \times 10^{-4}$ | 74.5 |

From the absorbance at 406 nm before and after addition of base the concentration of ester remaining and the percent ester reacted were determined for the reaction mixtures. The results show that the reaction rate is essentially linear over a 15 minute period.

At 15 minutes of reaction time, the reaction was stopped by applying the reaction mixture to a PD10 desalting Sephadex G-25 column (Pharmacia, Inc.) equilibrated with 0.1M phosphate buffer at pH 6.0. It was found that $2.6 \times 10^{-3}$ moles/l of the ester had reacted and thus 25.9% of the 59 epsilon-amino groups of BSA were presumably substituted. Thus, the product contained 16 mal-sac groups per molecule.

The product of the first reaction, mal-sac-BSA (or mal-sac-KLH), was isolated by applying the reaction mixture to a PD10 desalting Sephadex G-25 column equilibrated with 0.1M phosphate buffer at pH 6.0. The column was eluted with 0.1M phosphate buffer in 1.0 ml fractions. The column elution was followed by monitoring the absorbance spectrum, and peak fractions containing the mal-sac-BSA were pooled. cGAP 13 or peptide 891 synthesized as described above are added and the pooled mixture is stirred at room temperature overnight. The conjugates are subjected to extensive dialysis against distilled water and lyophilization, and in some cases are analyzed for changes in amino acid composition.

New Zealand white rabbits are immunized with the KLH derivatives of the peptides by peripheral lymph node injection in Freund Complete Adjuvant followed a few weeks later by subcutaneous (sub. q.) injection in Freund Incomplete Adjuvant. Three additional sub. q. injections are given at several week intervals. One or more month later intravenous boosts are given a few days apart and the serum sample taken several days later.

It will be appreciated by those skilled in the art that monoclonal antibodies to the above peptides are produced by means of hybridoma technique, as described in this "Detailed Description of the Invention."

Diagnostic Use of Antibodies

The antibodies described above can be employed in assaying for the presence of ras p21 protein, especially in tumors with an over expression of ras p21 protein. The availability of large amounts of these antibodies will thus be a valuable addition to present cancer diagnostic methods. Antibodies to cGAP 13 and peptide 891 are used. However, it will be appreciated by those skilled in the art that any antibodies to the following are usable in the assay: fragments of peptide 891 or cGAP 13 which retain the ability for binding to the ras p21protein, ras p21-GDP complex, or ras p21-GTP complex; and any peptide which competes with peptide 891 or cGAP 13 for binding to ras p21 protein, ras p21-GDP complex, or ras p21GTP complex.

An example of the assay method is by means of peptide 891, labelled p21 protein, and antibody to peptide 891. The antibodies to peptide 891 are bound to a solid support. They can be immobilized on any of the common supports used in immunometric assays. Among these are filter paper, plastic beads or test tubes made from polyethylene, polystyrene, polypropylene or other suitable materials. Also useful are particulate materials such as agarose, crosslinked dextran, and other polysaccharides. The techniques for such bonding are well known to those skilled in the art. For example, antibodies can be bound to polysaccharide polymers using the process described in U.S. Pat. No. 3,645,852.

The procedure for labelling of p21 is as described previously for the diagnostic uses of the peptide sequences. Sample of labelled p21 protein and peptide 891 are incubated to form a conjugate of peptide 891 and p21. A suspension of antibody immobilized on agarose particles is then added and the mixture is allowed to incubate in order to form an antibody-peptide 891p21 complex. Following the incubation periods, the agarose particles are washed by addition of buffer and centrifuged. After removal of the washing liquid by aspiration, the resulting pellet of agarose particles is then counted for bound labelled p21. The control for this experiment follows the same procedure but uses a known amount of labelled p21. The determination of the amount of p21 in the sample is arrived at by comparing the resulting radioactive counts of the control and the sample.

It will be appreciated by those skilled in the art that other assaying methods can be used. For example, the ras p21 protein is labelled with an enzyme or a fluorogenic material and examined by enzymatic or fluorometric means.

Methods for Using the Peptides in Treatment of Human Cancer

Administering peptides to the ras oncogenic transformed cells can revert their oncogenic behavior. The optimal dosage will revert the tumor cells to normal, but will have minimal or no adverse effect on normal cells. Therefore, as another feature of this invention, there is also disclosed methods of administering to a human the peptides or the peptides conjugated to a ligand (hereinafter refer to as peptide-ligand) to treat tumors caused by ras oncogenes. Examples of the ligand are antibody or peptide which recognize the ras oncogenic transformed cells. The conjugation is carried out according to procedures known in the art. An example of the procedure is described in detail in U.S. Pat. No. 4,340,535 which is hereby incorporated in whole.

The strategy used in treating a particular individual depends on the status of the individual and the objective of the treatment. The dosage varies with such factors as the size and age of the individual, stage of the disease, the concurrent treatments being given, e.g. radiotherapy, and the type of peptide or peptide-ligand used. In any treatment, the peptide or peptide-ligand must be administered to individuals in a manner capable of getting an effective dose into the blood stream and subsequently to the tumor cells to revert them to normal.

The peptide or peptide-ligand is administered by any suitable route including oral, rectal, nasal, topical (including buccal and sublingual), vaginal and parenteral (including subcutaneous, intramuscular, intravenous, intra-arterial and intradermal). Examples are intravenous injection and desirable blood levels may be maintained by a continuous infusion or by intermittent infusions. It will be appreciated that the preferred route may vary based on the factors discussed in the previous paragraph.

The peptide or peptide-ligand may be used in therapy in conjunction with other medicaments or radiotherapy. The peptide or peptide-ligand may be presented as part of a pharmaceutical formulation. The formulations of the present invention comprise at least one administered ingredient, i.e., a peptide or peptide-ligand, together with one or more acceptable carriers thereof and optionally other therapeutic ingredients. The carrier(s) must be "acceptable" in the sense of being compatible with the other ingredients of the formulation and not deleterious to the recipient. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The following is an example of the procedure: the patient is administered intravenous infusion of the peptide or peptide-ligand in a physiologically acceptable carrier at a starting dose of 2.0–20 mg/m² daily for five days. By reverting the oncogenic cells to normal, the peptide or peptide-ligand prevents the over proliferation of the cells. Thus, the tumor stops growing. Further, the cells which have reverted to normal, but still containing the ras oncogenes, are killed by chemotherapy and/or radiotherapy administered in conjunction with the peptide or peptide-ligand treatment. At the end of the five-day period, the patient is evaluated. The evaluation includes physical examination and extensive laboratory testing. The tests include evaluation for toxicity and specific tests directed to the particular tumor involved. For example, in the case of leukerna, the tests include determination of white blood cell count. If the patient's condition is stable, he is re-treated at the same dosage twice per week and evaluated weekly. Provided the patient's condition is stable, the treatment is continued for five months. At the end of the five month period, the patient is again evaluated and x-rayed. Comparison of the pre-treatment and post-treatment x-ray photographs indicates the efficacy of the combined treatments by showing whether the tumor has grown further or reduced in size. According to the efficacy of the combined treatments, and the patient's condition, the peptide or peptide-ligand dosage, the chemotherapy and/or radiotherapy may be increased or maintained constant for the duration of treatment. The patient's condition and the status of the tumor is monitored periodically through physical exam, laboratory test and x-ray. The starting dose of peptide or peptide-ligand, chemotherapy and/or radiotherapy is reduced for a patient who exhibits adverse reaction.

The formulations of this invention may include other agents conventional in the art having regard to the type of formulation in question. Further, the above treatment methods are by way of example, and do not preclude those known by persons skilled in the art.

Deposit of Biological Materials: The following plasmids have been deposited with the American Type Culture Collection 12301 Parklawn Drive, Rockville Md. 20852, on Oct. 11, 1988.

| Designation | ATCC No. | CMCC No. |
| --- | --- | --- |
| pAcC GAP 5 (pAcCl2 GAP 5) | 67821 | 3437 |
| pGAP 16-4 (Clone 16) | 40503 | 3479 |
| pGAP-SLE1 (Clone Sleepy) | 40504 | 3480 |

Having generally described the invention, it will be appreciated that the scope of the invention is limited only by the appended claims, and not by the particular materials and methods described above.

We claim:

1. A peptide which binds to the ras p21-GTP complex, comprising a GTPase activating protein (GAP) fragment of the following amino acid sequence: Met-Arg-Thr-Arg-Val-Val-Ser-Gly-Phe-Val-Phe-Leu-Arg-Leu-Ile-Cys, said peptide having a molecular weight of about 35,000 daltons or less.

2. A peptide that binds to ras p21-GTP complex, comprising a GTPase activating protein (GAP) fragment of the following amino acid sequence: Thr-Met-Arg-Thr-Arg-Val-Val-Ser-Gly-Phe-Val-Phe-Leu-Arg-Leu-Ile-Cys, said peptide having a molecular weight of about 35,000 daltons or less.

3. A GAP derived peptide which binds to ras p21-GDP complex and mediates a dissociation of GDP from said complex, said peptide comprising an amino acid sequence selected from the group consisting of: Thr-Met-Arg-Thr-Arg-Val-Val-Ser-Gly-Phe-Val-Phe-Leu-Arg-Leu-Ile-Cys and Met-Arg-Thr-Arg-Val-Val-Ser-Gly-Phe-Val-Phe-Leu-Arg-Leu-Ile-Cys, said peptide having a molecular weight of about 35,000 daltons or less.

4. The GAP derived peptide of claim 3 which is a GAP fragment having a molecular weight of about 35,000 daltons.

5. A peptide comprising a GTPase activating protein (GAP) fragment having an amino acid sequence selected from the group consisting of: Thr-Met-Arg-Thr-Arg-Val-Val-Ser-Gly-Phe-Val-Phe-Leu-Arg-Leu-Ile-Cys; and Met-Arg-Thr-Arg-Val-Val-Ser-Gly-Phe-Val-Phe-Leu-Arg-Leu-Ile-Cys, said peptide having a molecular weight of about 35,000 daltons or less.

6. A fragment of the peptide of claim 5, which retains the ability to bind ras p21-GTP complex.

7. A fragment of the peptide of claim 5, which retains the ability to inhibit GAP stimulated ras p21 GTPase activity.

8. A fragment of the peptide of claim 5, which competes with the peptide of claim 5 for binding to ras p21-GTP complex and which inhibits GAP stimulated ras p21 GTPase activity.

9. A peptide which inhibits GAP stimulated ras p21 GTPase activity, wherein said peptide is a fragment of a GAP comprising an amino acid sequence selected from the group consisting of: Thr-Met-Arg-Thr-Arg-Val-Val-Ser-Gly-Phe-Val-Phe-Leu-Arg-Leu-Ile-Cys; and Met-Arg-Thr-Arg-Val-Val-Ser-Gly-Phe-Val-Phe-Leu-Arg-Leu-Ile-Cys.

10. A GAP-derived peptide which inhibits GAP stimulated ras p21 GTPase activity.

11. The GAP-derived peptide of claim 10, wherein said peptide comprises about 16 amino acids.

12. The GAP-derived peptide of claim 10, which competes with a second peptide for binding to ras p21-GTP complex; wherein the second peptide has a molecular weight of about 35,000 daltons or less and comprises a fragment of GAP selected from the group consisting of: Thr-Met-Arg-Thr-Arg-Val-Val-Ser-Gly-Phe-Val-Phe-Leu-Arg-Leu-Ile-Cys; and Met-Arg-Thr-Arg-Val-Val-Ser-Gly-Phe-Val-Phe-Leu-Arg-Leu-Ile-Cys.

13. The GAP-derived peptide of claim 10, having a molecular weight of about 35,000 daltons or less.

14. The GAP-derived peptide of claim 12, comprising a fragment of GAP selected from the group consisting of: Thr-Met-Arg-Thr-Arg-Val-Val-Ser-Gly-Phe-Val-Phe-Leu-Arg-Leu-Ile-Cys; and Met-Arg-Thr-Arg-Val-Val-Ser-Gly-Phe-Val-Phe-Leu-Arg-Leu-Ile-Cys.

15. The GAP-derived peptide of claim 12, having a molecular weight of about 35,000 daltons or less.

16. A peptide of the following amino acid sequence: Thr-Met-Arg-Thr-Arg-Val-Val-Ser-Gly-Phe-Val-Phe-Leu-Arg-Leu-Ile-Cys.

17. A peptide of the following amino acid sequence: Met-Arg-Thr-Arg-Val-Val-Ser-Gly-Phe-Val-Phe-Leu-Arg-Leu-Ile-Cys.

* * * * *